(12) United States Patent
Hiroshima et al.

(10) Patent No.: US 10,398,384 B2
(45) Date of Patent: *Sep. 3, 2019

(54) PULSIMETER AND ADJUSTMENT METHOD OF PULSIMETER

(71) Applicant: Renesas Electronics Corporation, Kou-tou-ku, Tokyo (JP)

(72) Inventors: Akane Hiroshima, Tokyo (JP); Yuji Shimizu, Tokyo (JP)

(73) Assignee: RENESAS ELECTRONICS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/054,321

(22) Filed: Aug. 3, 2018

(65) Prior Publication Data
US 2018/0344258 A1 Dec. 6, 2018

Related U.S. Application Data

(63) Continuation of application No. 15/094,345, filed on Apr. 8, 2016, now Pat. No. 10,058,289.

(30) Foreign Application Priority Data

May 15, 2015 (JP) .................................. 2015-099747

(51) Int. Cl.
*A61B 5/00* (2006.01)
*A61B 5/024* (2006.01)

(52) U.S. Cl.
CPC ........ *A61B 5/7225* (2013.01); *A61B 5/02433* (2013.01); *A61B 5/6826* (2013.01); *A61B 2560/0209* (2013.01)

(58) Field of Classification Search
CPC . A61B 5/7225; A61B 5/02433; A61B 5/6826; A61B 2560/0209
See application file for complete search history.

(56) References Cited

U.S. PATENT DOCUMENTS 7,313,426 B2 12/2007 Takeda et al.
10,058,289 B2 * 8/2018 Hiroshima ........... A61B 5/7225
(Continued)

FOREIGN PATENT DOCUMENTS

| JP | 2005278758 A | 10/2005 |
|----|--------------|---------|
| JP | 2012183139 A | 9/2012 |
| JP | 2014076273 A | 5/2014 |

OTHER PUBLICATIONS

Communication dated Oct. 9, 2018 from the Japanese Patent Office in counterpart application No. 2015-099747.

*Primary Examiner* — Paula J Stice
(74) *Attorney, Agent, or Firm* — McDermott Will & Emery LLP

(57) ABSTRACT

It is possible to reduce power consumption of a pulsimeter while suppressing a degradation in an accuracy of measuring pulse. A pulsimeter (1) includes a light emitter (10), a photodetector (12), an AD converter (14), a frequency analyzing unit (15), and an adjusting unit (17). The light emitter (10) emits light to a blood vessel of a measurement target. The photodetector (12) detects light emitted by the light emitter (10) via the blood vessel. The AD converter (14) analog/digital converts an output signal of the photodetector (12). The frequency analyzing unit (15) frequency-analyzes data converted by the AD converter (14). The adjusting unit (17) adjusts an amount of light emitted by the light emitter (10) based on the analysis result by the frequency analyzing unit (15).

16 Claims, 15 Drawing Sheets

(56) References Cited

U.S. PATENT DOCUMENTS

| | | |
|---|---|---|
| 2014/0081153 A1 | 3/2014 | Kuno |
| 2014/0243626 A1 | 8/2014 | Krishnan et al. |
| 2014/0275850 A1 | 9/2014 | Venkatraman et al. |

\* cited by examiner

PULSIMETER AND ADJUSTMENT METHOD OF PULSIMETER

CROSS-REFERENCE TO RELATED APPLICATIONS

This application is a continuation application of U.S. patent application Ser. No. 15/094,345, filed Apr. 8, 2016, now U.S. Pat. No. 10,058,289, issued Aug. 28, 2018, which is based upon and claims the benefit of priority from Japanese patent application No. 2015-099747, filed on May 15, 2015, the disclosure of which is incorporated herein in its entirety by reference.

BACKGROUND

The present invention relates to a pulsimeter and an adjustment method of a pulsimeter, and relates to, for example, a pulsimeter and an adjustment method of a pulsimeter that emits light to a blood vessel.

A pulsimeter that uses a light emitter such as a light emitting diode (LED) and a photodetector such as a photo transistor or a photodiode is known. In general, the pulsimeter is configured to be driven by a battery, which means it is required to suppress power consumption.

A technique for suppressing power consumption in the LED to suppress power consumption in a measurement apparatus that emits light to a blood vessel is known. For example, Japanese Unexamined Patent Application Publication No. 2005-278758 discloses the following configuration as an apparatus for measuring concentrations of light absorbing substances in blood capable of achieving power saving. That is, an apparatus for measuring concentrations of light absorbing substances in blood in which a light receiving means receives light having different wavelengths emitted to a living tissue including a blood vessel from a plurality of light emitting means, the pulse wave obtained from the light receiving means is processed and the concentrations of light absorbing substances in blood are obtained, and a current optimizing means for controlling a drive current of the plurality of light emitting means to make AC components of the pulse wave have a predetermined value is disclosed.

SUMMARY

According to the technique disclosed in Japanese Unexamined Patent Application Publication No. 2005-278758, the drive current of the LED is controlled by the amplitude of the light-received signal. However, the light-received signal includes, besides the pulsation signal components, noise components. The amplitude of the noise components is larger than the amplitude of the pulsation signal components. Therefore, when the drive current of the LED is controlled by only the amplitude of the light-received signal, the amount of light of the LED required to measure the pulsation signal components may not be appropriately secured.

For example, when the amount of light is adjusted based on only the amplitude of the light-received signal, even when it is required to increase the amount of light to measure pulsation signal components, the magnitude of the amplitude of the light-received signal may be determined to be sufficient due to the presence of signal components other than the pulsation signal components. As a result, even though it is required to increase the amount of light, the amount of light is not increased or the amount of light is decreased, which causes a degradation in the measurement accuracy.

The other problems of the related art and the novel characteristics of the present invention will be made apparent from the descriptions of the specification and the accompanying drawings.

According to one embodiment, a pulsimeter includes an adjusting unit that adjusts an amount of light of a light emitter based on a result of frequency-analyzing data converted by an analog/digital converter.

According to the embodiment, it is possible to reduce power consumption of the pulsimeter while suppressing a degradation in the accuracy of measuring the pulse.

BRIEF DESCRIPTION OF THE DRAWINGS

The above and other aspects, advantages and features will be more apparent from the following description of certain embodiments taken in conjunction with the accompanying drawings, in which.

DETAILED DESCRIPTION

Figure 1:
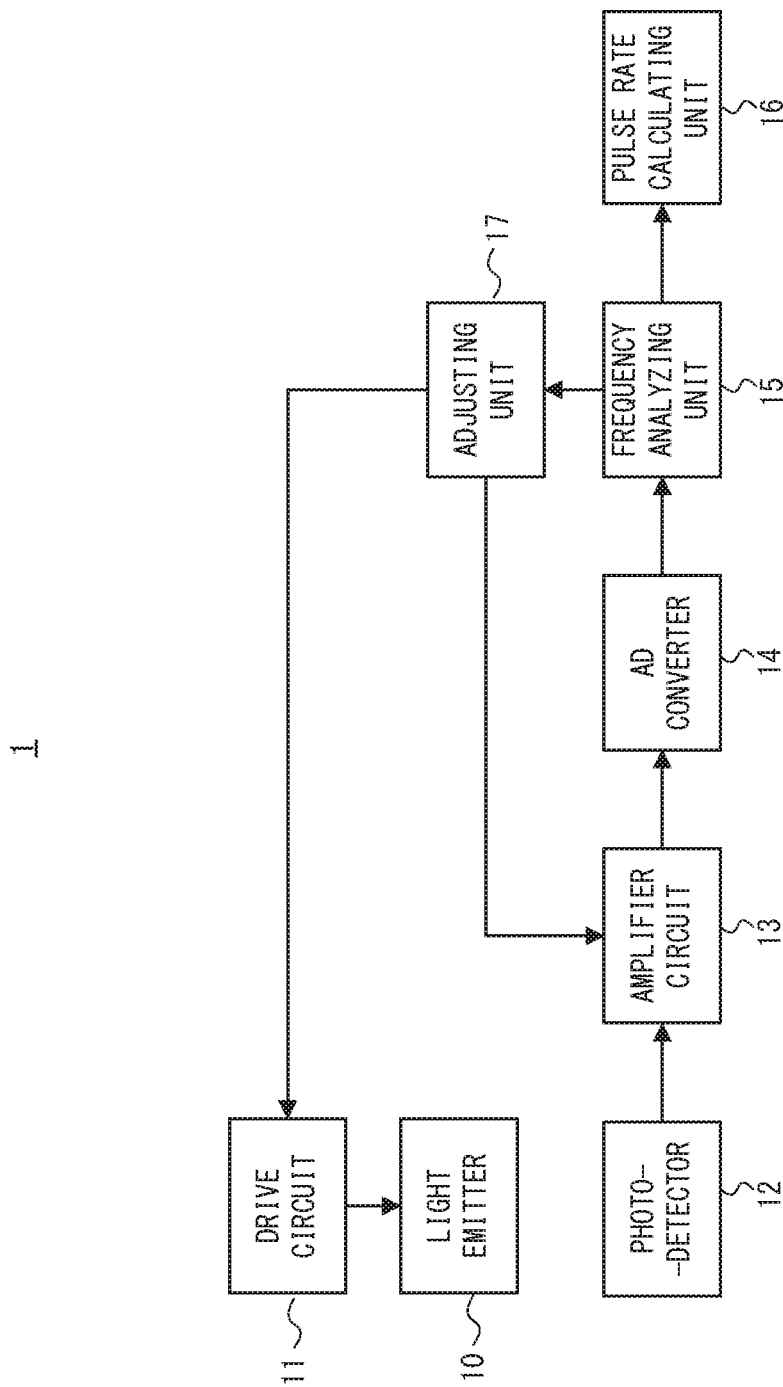
FIG. 1 is a block diagram showing a configuration of a pulsimeter according to a first embodiment.

For the clarification of the description, the following description and the drawings may be omitted or simplified as appropriate. Further, each element shown in the drawings as functional blocks that perform various processing can be formed of a CPU, a memory, and other circuits in hardware and may be implemented by programs loaded in the memory in software. Those skilled in the art will therefore understand that these functional blocks may be implemented in various ways by only hardware, only software, or the combination thereof without any limitation. Throughout the drawings, the same components are denoted by the same reference symbols and overlapping descriptions will be omitted as appropriate.

Further, the above program can be stored and provided to a computer using any type of non-transitory computer readable media. Non-transitory computer readable media include any type of tangible storage media. Examples of non-transitory computer readable media include magnetic storage media (such as flexible disks, magnetic tapes, hard disk drives, etc.), optical magnetic storage media (e.g., magneto-optical disks), Compact Disc Read Only Memory (CD-ROM), CD-R, CD-R/W, and semiconductor memories (such as mask ROM, Programmable ROM (PROM), Erasable PROM (EPROM), flash ROM, Random Access Memory (RAM), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

First Embodiment

FIG. 1 is a block diagram showing a configuration of a pulsimeter 1 according to this embodiment. The pulsimeter 1 includes a light emitter 10, a drive circuit 11, a photodetector 12, an amplifier circuit 13, an AD converter 14 (analog/digital converter), a frequency analyzing unit 15, a pulse rate calculating unit 16, and an adjusting unit 17.

The light emitter 10 is, for example, an LED. The light emitter 10 is driven by the drive circuit 11 and emits light. When the pulse is measured, the light emitter 10 emits light to a blood vessel of a subject. The light emitter 10 may include one or a plurality of LEDs. The light emitted by the light emitter 10 may have a desired color (e.g., green, red, infrared color). In this embodiment, the light emitter 10 is formed of two LEDs that emit green light.

The drive circuit 11 controls the amount of light and the timing of light emission when the light emitter 10 emits light. In this embodiment, the drive circuit 11 concurrently lights up or extinguishes two LEDs that emit green light. The drive circuit 11 controls the LEDs so that lighting and extinguishing are alternately repeated at a constant cycle. The strength of the light reflected from a human body varies due to a difference in the color of the skin, the thickness of the skin, etc. It is therefore required to adjust the amount of light according to the subject when the pulse is measured. The drive circuit 11 controls light emission of the light emitter 10 according to an instruction by the adjusting unit 17 described below. The drive circuit 11 is able to convert, for example, a digital control signal output from the adjusting unit 17 into an analog signal by a DA converter (digital/analog converter) and adjust the amount of light emitted by the light emitter 10.

Figure 2:
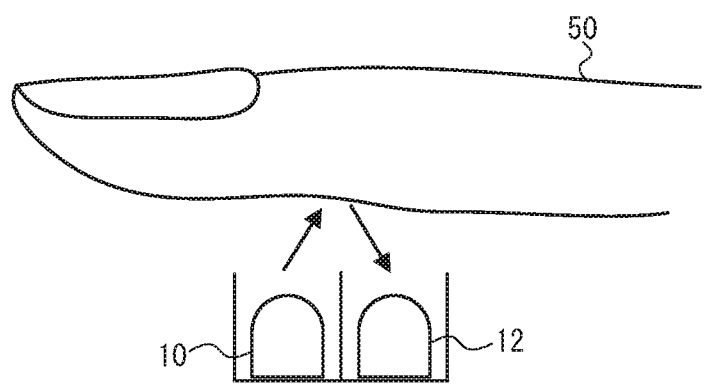
FIG. 2 is a schematic view showing a state in which a pulsation signal is acquired by a light emitter and a photodetector.

The photodetector 12 is formed of, for example, a photo transistor or a photodiode. The photodetector 12 detects light emitted by the light emitter 10 via the blood vessel of the subject when the pulse is measured. In this embodiment, as shown in FIG. 2, the light emitter 10 and the photodetector 12 are arranged in such a way that they are directed in the same direction with respect to a part of the human body (a finger 50 in the example shown in FIG. 2) of the subject. Therefore, the photodetector 12 detects light obtained by reflecting the light emitted by the light emitter 10 by the part of the human body of the subject. That is, when the pulse is measured, the photodetector 12 detects light obtained by reflecting the light emitted by the light emitter 10 in the blood vessel of the subject. The part of the human body illuminated by the light emitted by the light emitter 10 is not limited to the finger and may be, for example, an arm. When the reflective sensor is used as described above, there is no need to provide the light emitter and the photodetector so that they are opposed to each other with the human body interposed therebetween, whereby it is possible to reduce the size of the device. Further, since the configuration in which the pulse is measured by emitting the light to the human body is employed in this embodiment, the burden on the subject is reduced.

The strength of the light detected by the photodetector 12 fluctuates according to the pulsation in the blood vessel. As will be described later, the pulsimeter 1 calculates the pulse rate by capturing this fluctuation.

The amplifier circuit 13 amplifies an output signal of the photodetector 12. The amplifier circuit 13 includes a programmable instrumentation amplifier and the gain of the amplifier circuit 13 can be changed. Further, the amplifier circuit 13 includes a differential amplifier circuit, cancels a DC offset signal that will be described below, and amplifies a pulsation signal. Specifically, a voltage indicating a biometric signal acquired via the photodetector 12 and a bias voltage to cancel the DC offset signal are input to the differential amplifier circuit as input signals. The signal amplified by the amplifier circuit 13 is input to the AD converter 14.

The AD converter 14 analog/digital converts the output signal of the photodetector 12. More specifically, the AD converter 14 analog/digital converts the signal amplified by the amplifier circuit 13 at a constant cycle. In this way, the analog signal output from the amplifier circuit 13 is converted into digital data, which is sampling data for calculating the pulse rate. When the measurement is started, light emission by the light emitter 10 is repeated, which causes the AD converter 14 to successively output the sampling data.

The frequency analyzing unit 15 frequency-analyzes data converted by the AD converter 14. Every time a predetermined pieces of sampling data is input to the frequency analyzing unit 15 from the AD converter 14, the frequency analyzing unit 15 frequency-analyzes a data series formed of the predetermined pieces of sampling data. Specifically, the frequency analyzing unit 15 carries out Fast Fourier Transform (FFT) processing on the data series of the sampling data at a predetermined cycle. The frequency analyzing unit 15 outputs the result of the analysis to the pulse rate calculating unit 16 and the adjusting unit 17.

The pulse rate calculating unit 16 calculates the pulse rate from the result of the analysis by the frequency analyzing unit 15. Specifically, the pulse rate calculating unit 16 extracts, from frequency components of a frequency band (e.g., 0.5 Hz-2 Hz) corresponding to the pulse analyzed by the frequency analyzing unit 15, the frequency component whose spectral value is the largest as a frequency corresponding to the pulse and calculates the pulse rate from the frequency that has been extracted. The pulse rate is calculated by converting the frequency that has been extracted into the frequency of vibrations per minute.

The adjusting unit 17 adjusts the amount of light emitted by the light emitter 10 and the gain of the amplifier circuit 13 based on the result of the analysis by the frequency analyzing unit 15. Further, the adjusting unit 17 adjusts the bias voltage to be input to the amplifier circuit 13 to the bias voltage according to the signal strength of the DC offset signal based on the result of the analysis by the frequency analyzing unit 15.

Now, the adjustment of the amount of light emitted by the light emitter 10 and the adjustment of the gain of the amplifier circuit 13 will be described. In the pulsimeter 1, in order to appropriately measure the pulse, the amount of light emitted by the light emitter 10 or the gain of the amplifier circuit 13 needs to be adjusted by the magnitude of the pulsation signal to be detected. However, the biometric signal acquired via the photodetector 12 includes, besides the biometric signal (pulsation signal) indicating pulse information, a biometric signal obtained by the reflection of light in sites other than the pulse (e.g., skin, bone). The value of the biometric signal obtained by the reflection of light in the sites other than the pulse becomes larger than the value of the pulsation signal. In particular, when the reflective sensor as shown in FIG. 2 is used, the biometric signal obtained by the reflection of light in the sites other than the pulse significantly appears. In this example, the biometric signal obtained by the reflection of light in the sites other than the pulse is defined to be a DC offset signal.

When this DC offset signal is always constant, it is possible to easily extract only the pulsation signal from the biometric signal. However, the magnitude of the DC offset signal varies for each subject and fluctuates according to the state during the measurement, such as the posture of the subject during the measurement, the distance between the photodetector 12 and the measurement target, a lightness of a surrounding environment, etc. The fluctuation of the DC offset signal is expressed by a low-frequency signal and has a bandwidth that is close to that of the pulsation signal. Therefore, in order to achieve the process of removing only the fluctuation of the DC offset signal from the biometric signal and extracting the pulsation signal by filter processing, a high-dimensional filter processing is required. However, when such a filter is used, it takes time for the output of the filter to be stable, and the load by the calculation becomes large.

Figure 3A:
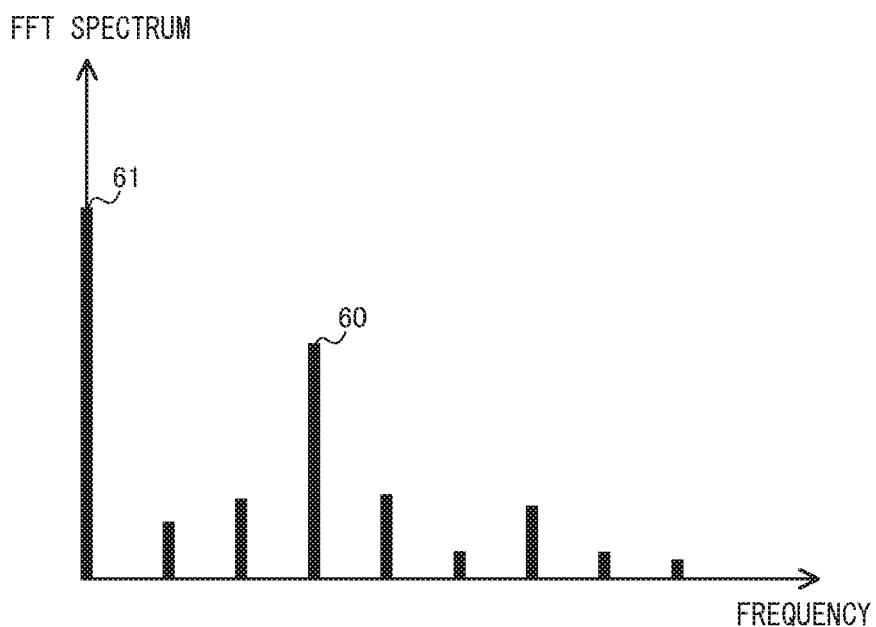
FIG. 3A is a graph showing an example of frequency analysis results by a frequency analyzing unit and shows an example of a case in which the magnitude of a frequency spectrum of the pulsation signal is smaller than a predetermined criterion.
Figure 3B:
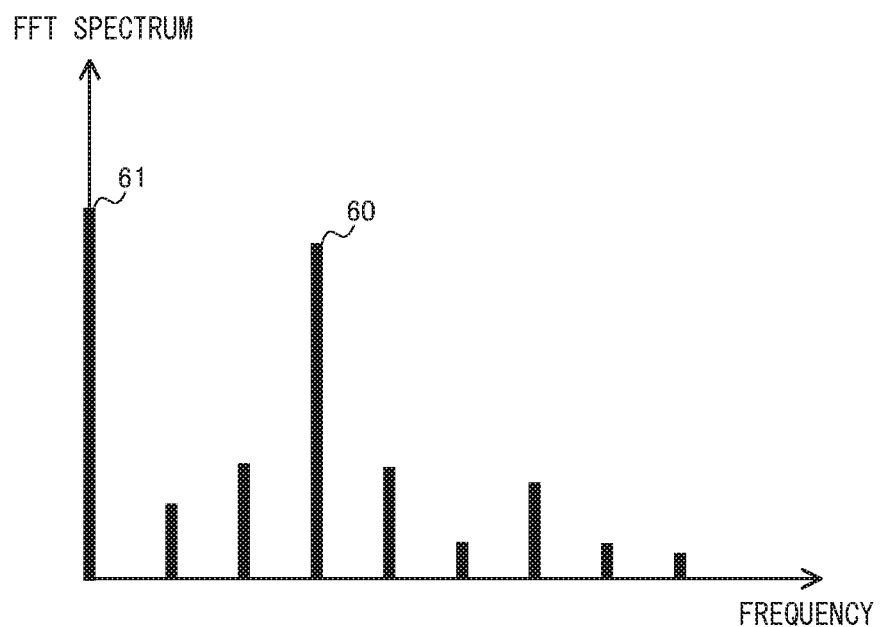
FIG. 3B is a graph showing an example of the frequency analysis results by the frequency analyzing unit and shows an example of a case in which the magnitude of the frequency spectrum of the pulsation signal is larger than the predetermined criterion.

In this embodiment, instead of extracting the pulsation signal by the filter processing, the pulsation signal is extracted based on the result of the analysis by the frequency analyzing unit 15 and the signal level of the pulsation signal is determined. FIGS. 3A and 3B are graphs each showing an example of the frequency analysis results by the frequency analyzing unit 15. FIG. 3A shows a case in which the magnitude of the frequency spectrum of the pulsation signal is smaller than a predetermined criterion and FIG. 3B shows a case in which the magnitude of the frequency spectrum of the pulsation signal is larger than the predetermined criterion. As described above, the pulse rate calculating unit 16 specifies the pulsation signal from the result of the analysis by the frequency analyzing unit 15 and calculates the pulse rate. Therefore, the pulse rate calculating unit 16 extracts, for example, a frequency component 60 having the largest spectral value (see FIGS. 3A and 3B) among the frequency components of the frequency band corresponding to the pulse analyzed by the frequency analyzing unit 15.

According to the frequency analysis by the frequency analyzing unit 15, as shown in FIGS. 3A and 3B, it is possible to obtain the signal strength (frequency spectrum) of each frequency component. That is, it is possible to easily obtain the signal strength of the pulsation signal from the result of the analysis by the frequency analyzing unit 15. The adjusting unit 17 acquires the signal strength of the pulsation signal from the result of the analysis by the frequency analyzing unit 15 and when the signal strength of the pulsation signal is smaller than a predetermined criterion, increases the amount of light emitted by the light emitter 10 to make it larger than the current amount of light or increases the gain of the amplifier circuit 13 to make it higher than the current gain. Further, the adjusting unit 17 acquires the signal strength of the pulsation signal from the result of the analysis by the frequency analyzing unit 15 and when the signal strength of the pulsation signal is equal to or larger than a predetermined criterion, decreases the amount of light emitted by the light emitter 10 to make it smaller than the current amount of light or decreases the gain of the amplifier circuit 13 to make it lower than the current gain.

More specifically, in this embodiment, the adjusting unit 17 operates as follows. The adjusting unit 17 calculates the noise level of the pulsation signal, that is, S/N ratio (signal-to-noise ratio) from the result of the analysis by the frequency analyzing unit 15, compares the S/N ratio with a predetermined threshold, and performs the adjustment according to the comparison result. The frequency components other than the frequency of the pulsation signal are defined to be noise. The adjusting unit 17 calculates the S/N ratio regarding the pulsation signal from the result of the analysis by the frequency analyzing unit 15. When the S/N ratio that has been calculated is equal to or larger than a predetermined threshold, the amount of light emitted by the light emitter 10 or the gain of the amplifier circuit 13 is reduced to indicate that the noise is small. Further, the adjusting unit 17 calculates the S/N ratio regarding the pulsation signal from the result of the analysis of the frequency analyzing unit 15, and when the S/N ratio that has been calculated is smaller than the predetermined threshold, the amount of light emitted by the light emitter 10 or the gain of the amplifier circuit 13 is increased to indicate that the noise is large. The adjusting unit 17 determines the set-up value to adjust the amount of light or the gain and carries out the adjustment every time the frequency analyzing unit 15 outputs the frequency analysis result. In this embodiment, when the adjusting unit 17 determines that the amount of light or the gain needs to be increased, for example, the adjusting unit 17 increases the set-up value of the amount of light or the set-up value of the gain by a predetermined fixed adjustment width. On the other hand, when the adjustment unit 17 determines that the amount of light or the gain needs to be decreased, the adjusting unit 17 decreases the set-up value of the amount of light or the set-up value of the gain by this fixed adjustment width.

As described above, by performing the adjustment by the adjusting unit 17, it is possible to suppress power consumption while keeping the measurement of the pulse.

Further, as shown in FIGS. 3A and 3B, from the result of the analysis by the frequency analyzing unit 15, the DC offset signal is obtained as the frequency components of a predetermined frequency band, more specifically, a frequency component 61 whose frequency is about 0 Hz. It is therefore possible to acquire the strength of the DC offset signal included in the biometric signal acquired via the photodetector 12 from the result of the analysis by the frequency analyzing unit 15. Therefore, the adjusting unit 17 acquires the signal strength of the DC offset signal based on the result of the analysis by the frequency analyzing unit 15. The adjusting unit 17 then adjusts the bias voltage to be input to the amplifier circuit 13 to the bias voltage according to the signal strength of the DC offset signal. It is therefore possible to cancel the DC offset signal from the signals output from the photodetector 12 in the amplifier circuit 13 and amplify the remaining signal components. It is therefore possible to improve the accuracy of measuring the pulse.

While the adjustment by the adjusting unit 17 according to this embodiment has been described above, the adjustment of the amount of light according to a comparative example will now be described. It is assumed that, in a pulsimeter according to the comparative example, the amount of light emitted by the light emitter 10 is adjusted based on only the amplitude of the signal received by the photodetector 12 (hereinafter this signal will be referred to as a light receiving signal). This light receiving signal corresponds to the above biometric signal. In this case, the pulsimeter according to the comparative example has the following problem.

Figure 4A:
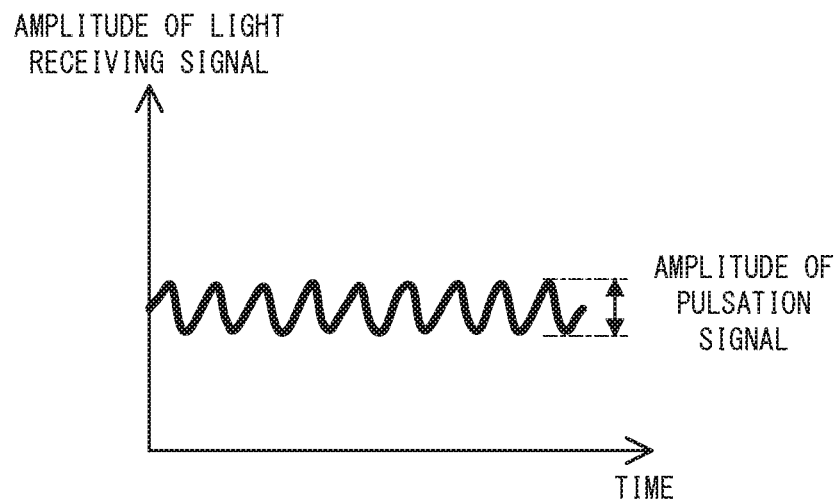
FIG. 4A is a graph showing an example of the amplitude of a light receiving signal in a pulsimeter according to a comparative example and shows an example of an amplitude when there is no noise in the light receiving signal.
Figure 4B:
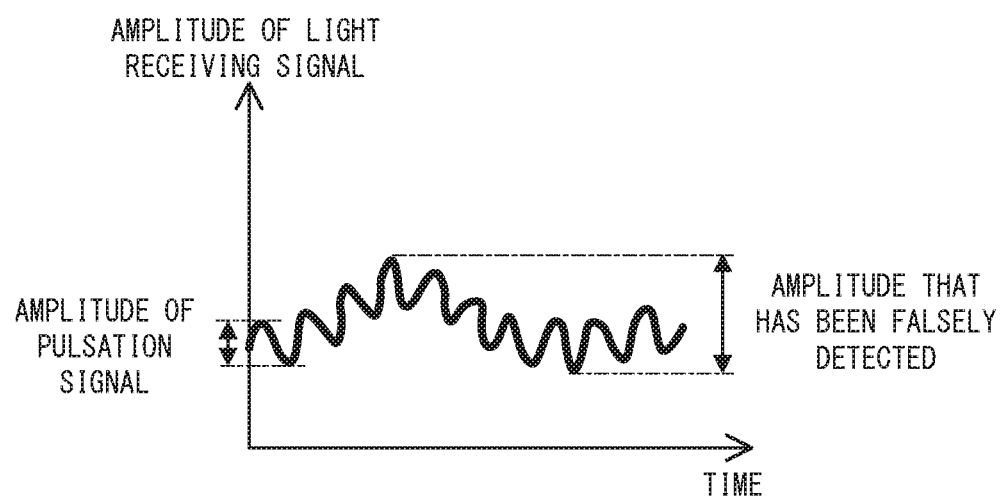
FIG. 4B is a graph showing an example of the amplitude of the light receiving signal in the pulsimeter according to the comparative example and shows an example of an amplitude when noise due to a body motion is included in the light receiving signal.

FIGS. 4A and 4B are graphs each showing an example of the amplitude of the light receiving signal in the pulsimeter according to the comparative example. FIG. 4A shows an example of the amplitude when there is no noise in the light receiving signal and FIG. 4B shows an example of the amplitude when the light receiving signal includes noise due to a body motion or the like. When there is no noise in the light receiving signal as shown in FIG. 4A, the pulse can be measured even when the amplitude of the pulsation signal is relatively small. In the pulsimeter according to the comparative example, however, the amount of light emitted by the light emitter 10 is adjusted by only the amplitude. Therefore, when the amplitude is small, even when the S/N ratio is high enough to measure the pulse, such an adjustment is performed to increase the amount of light. Therefore, the power consumption is unnecessarily increased. When the noise such as a body motion is included in the light receiving signal as shown in FIG. 4B, the amplitude of the pulsation signal may be falsely detected due to an influence of the noise. For example, the amplitude of the noise component due to the body motion is often larger than the amplitude of the pulsation signal. Therefore, when the amplitude due to the body motion is erroneously determined to be the amplitude of the pulsation signal, the amount of light may not be increased even when the amount of light is insufficient. In such a case, the amount of light is not sufficient and the pulsation signal cannot be measured.

On the other hand, in the adjustment according to this embodiment, the adjustment is performed based on the signal strength of the pulsation signal based on the result of the analysis by the frequency analyzing unit 15, whereby it is possible to reduce the erroneous adjustment due to the noise components. It is therefore possible to appropriately reduce the power consumption of the pulsimeter while suppressing the degradation of the accuracy of measuring the pulse. Further, since the amount of light emitted by the light emitter 10 or the gain of the amplifier circuit 13 is set from the frequency analysis results by the frequency analyzing unit 15, there is no need to provide the filter, which is used to extract only the pulsation signal from the light receiving signal, whereby the processing load can be suppressed. Since the frequency analysis by the frequency analyzing unit 15 is necessary to calculate the pulse rate by the pulse rate calculating unit 16, no additional load is applied to adjust the amount of light and the gain.

In this embodiment, the adjusting unit 17 increases or decreases the amount of light emitted by the light emitter 10 or the gain of the amplifier circuit 13 in either the case in which the S/N ratio that has been calculated is equal to or larger than a predetermined threshold or the case in which the S/N ratio that has been calculated is smaller than the predetermined threshold. However, this adjustment may be performed in one of the above cases. Further, the adjusting unit 17 may adjust only one of the amount of light emitted by the light emitter 10 and the gain of the amplifier circuit 13.

The frequency analyzing unit 15, the pulse rate calculating unit 16, and the adjusting unit 17 are implemented by a Micro Control Unit (MCU), for example. More specifically, the MCU is formed of a Central Processing Unit (CPU), a non-volatile memory or the like, programs corresponding to the frequency analyzing unit 15, the pulse rate calculating unit 16, and the adjusting unit 17 are stored in the non-volatile memory, and each of the processes is performed by executing the corresponding program by the CPU. The frequency analyzing unit 15, the pulse rate calculating unit 16, and the adjusting unit 17 may be processed by a main CPU and a sub CPU. Further, the amplifier circuit 13 and the AD converter 14 may be provided outside of the MCU or may be included in the MCU.

Second Embodiment

Next, a second embodiment will be described. A description of the components already described above will be omitted. The second embodiment is different from the first embodiment in that an adjustment width when the amount of light emitted by the light emitter 10 is adjusted is calculated. Accordingly, in this embodiment, when the adjusting unit 17 determines that an increase in the amount of light is required, for example, the adjustment unit 17 increases the amount of light by an amount corresponding to the adjustment width that has been calculated instead of increasing the amount of light by an amount corresponding to a fixed width which does not depend on the measurement environment.

When light is emitted by the light emitter 10 and the emitted light is received by the photodetector 12 via a finger or an arm, the amount of light that is received varies since the amount of light absorbed differs for each person. While there is a correlation between the amount of light emitted by the light emitter 10 and the amount of light received by the photodetector 12, this correlation is not necessarily a linear one and differs depending on conditions such as the thickness and the property of the skin of each person. It is therefore difficult to theoretically infer the relational expression in advance. Further, even when the light emitter 10 emits a constant amount of light, the amount of light received by the photodetector 12 varies depending on the measurement environment such as the distance between the photodetector 12 and the measurement target. Therefore, it is required to automatically and occasionally adjust the amount of light emitted by the light emitter 10. In the first embodiment, as described above, the amount of light emitted by the light emitter 10 is appropriately adjusted by monitoring the light-receiving state by the adjusting unit 17.

Figure 5:
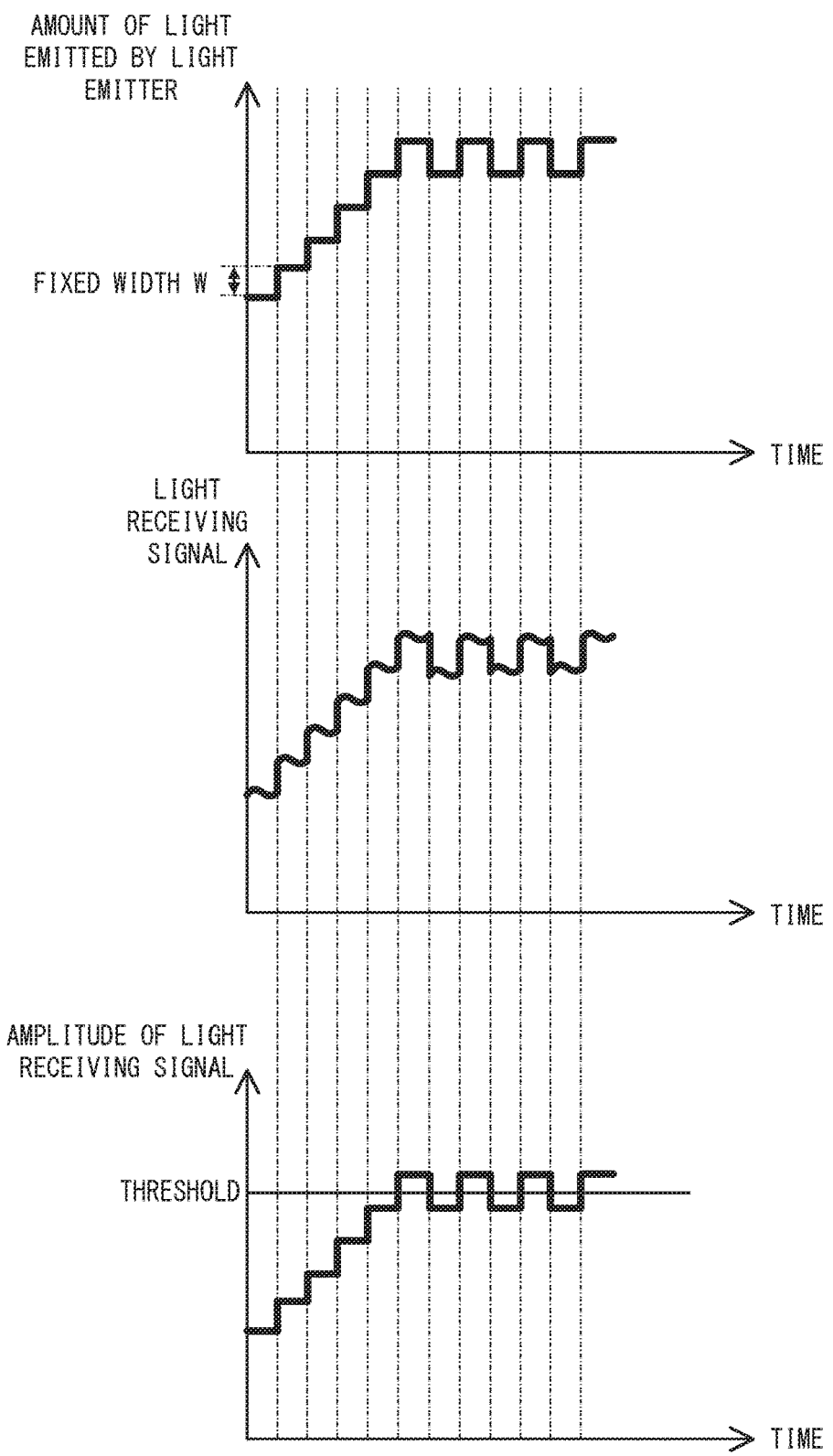
FIG. 5 is graphs showing an example of a state in which an amount of light is adjusted according to the comparative example, with an upper graph showing a temporal transition of the amount of light to be emitted, a middle graph showing a temporal transition of the light receiving signal to be detected, and a lower graph showing a temporal transition of the amplitude of the light receiving signal.

Now, a case in which the adjustment width of the set-up value of the amount of light is fixed will be described. FIG. 5 is graphs showing an example of a state in which the amount of light is adjusted according to the comparative example. The upper graph of FIG. 5 shows a temporal transition of the amount of light that is emitted, the middle graph of FIG. 5 shows a temporal transition of the light receiving signal to be detected, and the lower graph of FIG. 5 shows a temporal transition of the amplitude of the light receiving signal. In the comparative example shown in FIG. 5, the amount of light to be emitted is adjusted by a fixed adjustment width based on the result of comparing the amplitude of the light receiving signal with a threshold. That is, in the pulsimeter according to the comparative example, the adjustment width of the adjustment performed at a predetermined cycle is a fixed width. In other words, in each adjustment performed at a predetermined cycle, the adjustment width in one adjustment is a fixed width. At this time, as shown in FIG. 5, in the pulsimeter according to the comparative example, for each adjustment, the set-up value of the amount of light to be emitted is changed by a fixed width W. Therefore, in the pulsimeter according to the comparative example, when the amplitude of the light receiving signal is equal to or smaller than the threshold, the amount of light is increased by the fixed width W until the time the amplitude of the light receiving signal reaches the threshold. Further, in the pulsimeter according to the comparative example, when the amplitude of the light receiving signal exceeds the threshold, the amount of light is decreased at the fixed width W. As the fixed width W becomes smaller, the responsiveness when the amount of light is changed degrades. Therefore, when the amount of light is insufficient at an initial stage of the measurement, it takes time for the normal measurement to be started. On the other hand, when the fixed width W is too large, the amount of light becomes too large when the amount of light is increased, which may cause the AD converted value of the light receiving signal to be in a saturation state. In this case, the pulse information cannot be obtained.

In this embodiment, when the measurement is started, the relation between the amount of light that is emitted and the amount of light that is received is inferred by the measurement and the adjustment width of the amount of light emitted by the light emitter 10 is determined from the result of this inference. That is, the adjusting unit 17 calculates the amount of light to achieve a target evaluation value from a first evaluation value regarding the strength of the pulsation signal when the light emitter 10 emits light with a first amount of light, a second evaluation value regarding the strength of the pulsation signal when the light emitter 10 emits light with a second amount of light, and a predetermined target evaluation value regarding the strength of the pulsation signal. The adjusting unit 17 then adjusts the amount of light emitted by the light emitter 10 based on the calculation result. The target evaluation value is, for example, the S/N ratio regarding the pulsation signal that is required for stable measurement, and can be obtained by an experiment in advance.

Figure 6:
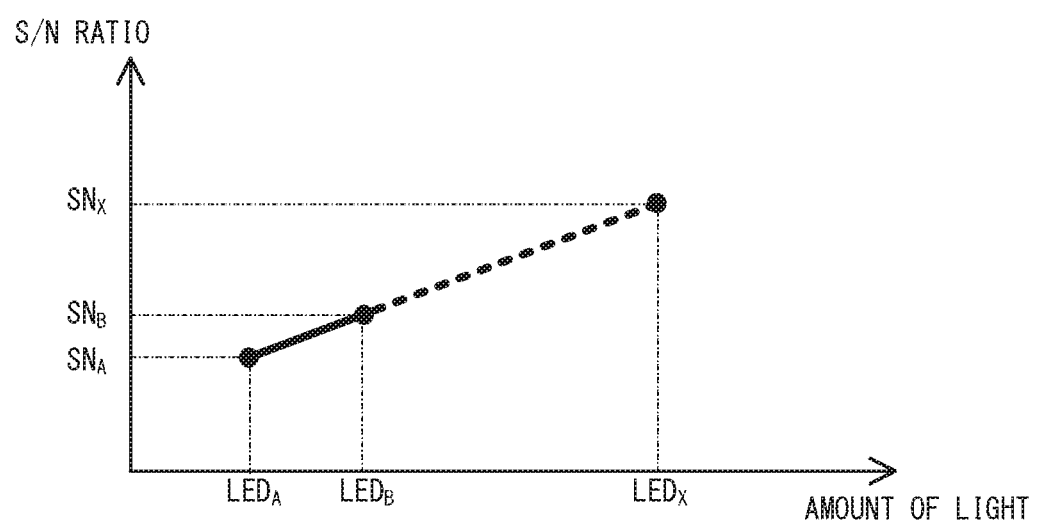
FIG. 6 is a diagram for describing a calculation of an adjustment width and shows a graph showing a relation between the amount of light emitted by the light emitter and an S/N ratio regarding the pulsation signal.

In this embodiment, the adjusting unit 17 specifically calculates the adjustment width of the amount of light emitted by the light emitter 10 as follows. FIG. 6 is a diagram for describing a calculation of the adjustment width according to this embodiment and shows a graph indicating a relation between the amount of light emitted by the light emitter 10 and the S/N ratio regarding the pulsation signal. In FIG. 6, $LED_A$ corresponds to the first amount of light, $LED_B$ corresponds to the second amount of light, $SN_A$ corresponds to the first evaluation value, $SN_B$ corresponds to the second evaluation value, and $SN_X$ corresponds to the target evaluation value.

First, the adjusting unit 17 causes the light emitter 10 to emit light with a desired amount of light and records the amount of light at this time ($LED_A$ in FIG. 6) and the S/N ratio regarding the pulsation signal ($SN_A$ in FIG. 6). Next, the adjusting unit 17 changes the amount of light at a predetermined fixed width and causes the light emitter 10 to emit light, and records the amount of light at this time ($LED_B$ in FIG. 6) and the S/N ratio regarding the pulsation signal ($SN_B$ in FIG. 6). Next, the adjusting unit 17 approximates the relation between the amount of light emitted by the light emitter 10 and the S/N ratio regarding the pulsation signal from the recorded results. That is, the above relation is approximated by a line having a slope k: $(SN_B-SN_A)/(LED_B-LED_A)$ and an intercept i:$SN_A-LED_A \times (SN_B-SN_A)/(LED_B-LED_A)$. The adjusting unit 17 then calculates the amount of light emitted by the light emitter 10 ($LED_X$ in FIG. 6) to achieve the target S/N ratio ($SN_X$ in FIG. 6). Specifically, the amount of light emitted by the light emitter 10 is calculated by $LED_X=(SN_X-\text{intercept i})/\text{slope k}$. The adjusting unit 17 adjusts the amount of light emitted by the light emitter 10 to cause the light emitter 10 to emit the calculated amount of light.

Figure 7:
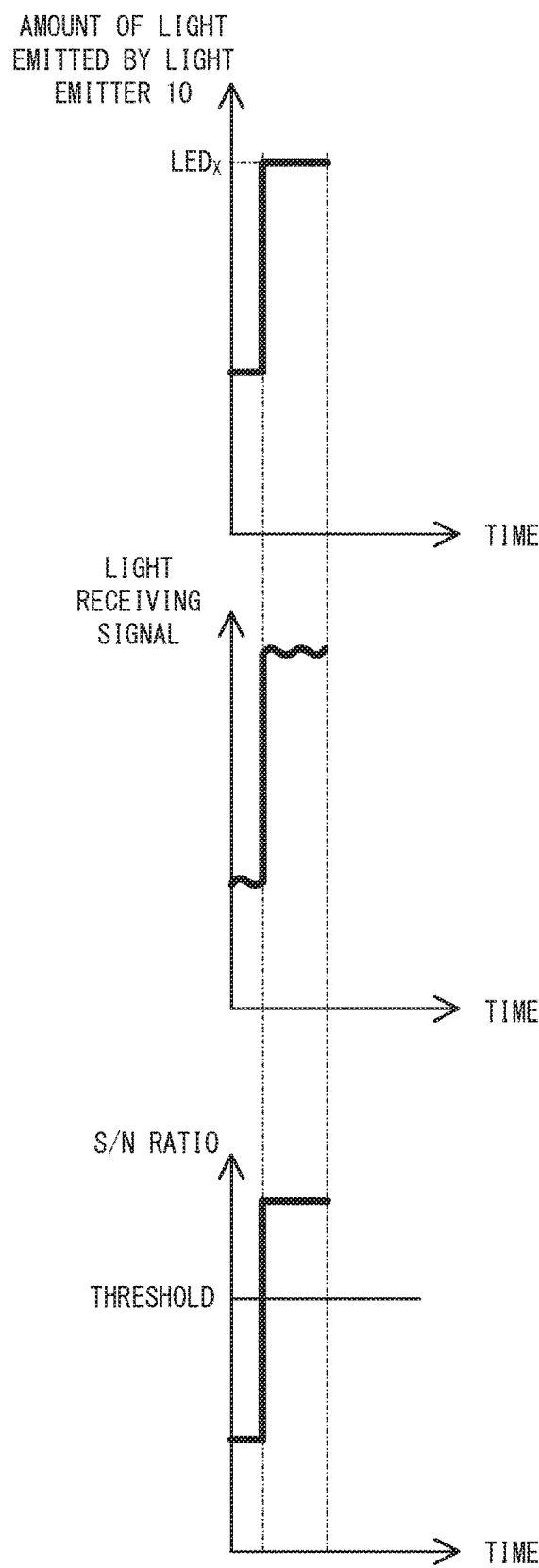
FIG. 7 is graphs showing an example of a state in which an amount of light is adjusted in a pulsimeter according to a second embodiment, with an upper graph showing a temporal transition of the amount of light to be emitted, a middle graph showing a temporal transition of the light receiving signal to be detected, and a lower graph showing a temporal transition of the S/N ratio of the pulsation signal that has been acquired.

As described above, in this embodiment, the adjustment width is calculated for each measurement environment, whereby it is possible to obtain the adjustment width suitable for the measurement environment. FIG. 7 is graphs showing one example of a state in which the amount of light is adjusted in the pulsimeter 1 according to this embodiment. The upper graph of FIG. 7 shows a temporal transition of the amount of light that is emitted, the middle graph of FIG. 7 shows a temporal transition of the light receiving signal to be detected, and the lower graph of FIG. 7 shows a temporal transition of the S/N ratio of the pulsation signal that has been acquired. In this embodiment, as shown in FIG. 7, the amount of light emitted by the light emitter 10 is adjusted to achieve the amount of light $LED_X$ that has been calculated, whereby it is possible to improve the responsiveness while suppressing the AD converted value of the light receiving signal from being the saturation state. Therefore, it is possible to reduce the time for the normal measurement to be started compared to the case in which this configuration is not included.

Third Embodiment

Next, a third embodiment will be described. A description of the components already described above will be omitted. In this embodiment, the adjustment width when the amount of light emitted by the light emitter 10 is adjusted is set to different values depending on whether the amount of light is adjusted to increase it or the amount of light is adjusted to decrease it. More specifically, in the pulsimeter 1 according to this embodiment, the adjustment width of the adjustment by the adjusting unit 17 performed at a predetermined cycle when the amount of light emitted by the light emitter 10 is adjusted to increase it is larger than the adjustment width of the adjustment by the adjusting unit 17 performed at the predetermined cycle when the amount of light emitted by the light emitter 10 is adjusted to decrease it. In other words, in each adjustment performed at the predetermined cycle, the adjustment width in one adjustment when the amount of light is increased is set to be larger than the adjustment width in one adjustment when the amount of light is decreased.

There are two purposes for changing the amount of light emitted by the light emitter 10. The first purpose is to increase the amount of light and appropriately acquire the pulse information when the biometric signal acquired in the photodetector 12 does not include the pulse information or will not include the pulse information since the amount of light emitted by the light emitter 10 is not sufficient. The second purpose is to suppress the amount of light emitted by the light emitter 10 and reduce the power consumption when the pulse can be normally measured.

Figure 8:
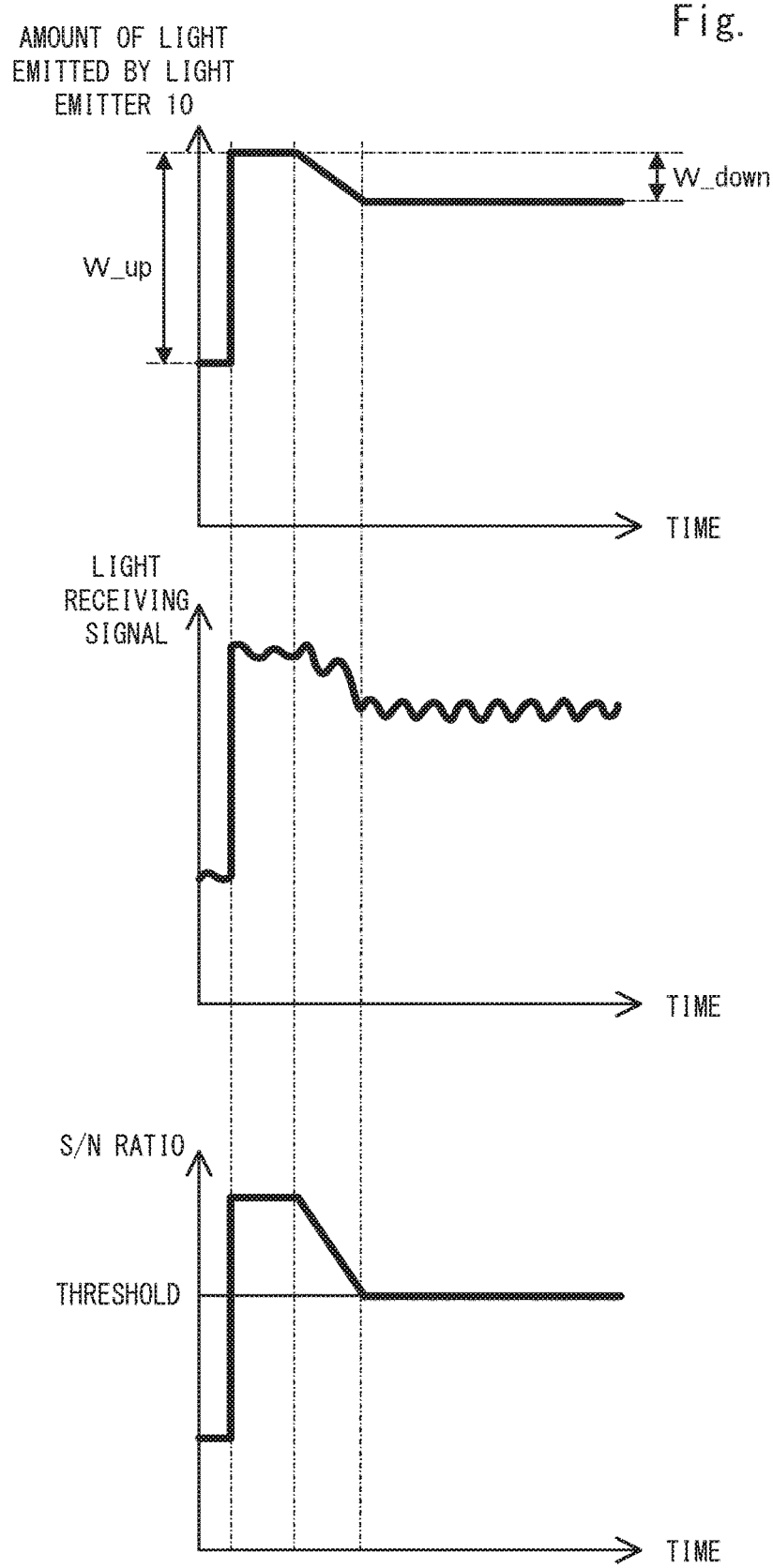
FIG. 8 is graphs showing an example of a state in which an amount of light is adjusted in a pulsimeter according to a third embodiment, with an upper graph showing a temporal transition of the amount of light to be emitted, a middle graph showing a temporal transition of the light receiving signal to be detected, and a lower graph showing a temporal transition of the S/N ratio of the pulsation signal that has been acquired.

Regarding the first purpose, the measurement cannot be performed or will not be performed. Therefore, the high response performance when the amount of light is increased is required. On the other hand, regarding the second purpose, the measurement has already been performed appropriately. Therefore, it is more important to maintain the state in which the measurement can be appropriately performed than the high response performance. When the adjustment by the adjusting unit 17 is performed, a distortion may occur in the pulsation signal waveform due to the adjustment. This distortion becomes larger as the adjustment width becomes larger. Therefore, regarding the second purpose, the adjustment width is preferably as small as possible. In view of the above discussion, in this embodiment, the adjusting unit 17 changes the adjustment width depending on whether the amount of light is adjusted to increase it or the amount of light is adjusted to decrease it. That is, as shown in FIG. 8, the adjusting unit 17 adjusts the amount of light by an adjustment width W_up when the amount of light is increased and adjusts the amount of light by an adjustment width W_down when the amount of light is decreased. The adjustment width W_up is larger than the adjustment width W_down. The adjustment width W_up may be, for example, a predetermined adjustment width or may be an adjustment width to adjust the amount of light to the amount of light that has been calculated as described in the second embodiment. Further, while it is sufficient that the adjustment width W_down be an adjustment width smaller than the adjustment width W_up, the adjustment width W_down is preferably a configurable minimum adjustment width, for example, to reduce the distortion of the signal waveform. Even when a distortion occurs in a signal waveform when the amount of light is increased when the measurement is not normally performed, this distortion does not cause any problem since the measurement is not normally performed in the first place. That is, since the data of the signal waveform including the distortion cannot be used for the calculation of the pulse rate, all the data should be discarded.

According to the pulsimeter 1 according to this embodiment, it is possible to achieve both the high response performance required for the measurement and the maintenance of the state in which the measurement is appropriately performed.

Fourth Embodiment

Next, a fourth embodiment will be described. A description of the components already described above will be omitted. In the adjustment of the amount of light emitted by the light emitter 10 or the adjustment to cancel the DC offset signal, when the adjustment are performed all at once regardless of the adjustment widths, a distortion may occur in the pulsation signal. If the adjustment timing is set to a cycle which does not have a relation with the pulsation signal, it is possible to remove a frequency generated by the adjustment when the frequency analysis is performed. However, considering that there is an influence of a folding frequency or the like, it is difficult to determine the adjustment timing. In this embodiment, the timing of the adjustment to suppress the distortion of the pulsation signal caused by the adjustment will be proposed.

In this embodiment, the adjusting unit 17 performs the adjustment by dividing the timings when the adjustment is performed. Specifically, the adjusting unit 17 according to this embodiment determines the set-up value for the adjustment at a predetermined cycle and executes the adjustment of the determined set-up value by a plurality of divided processes within the predetermined cycle. That is, the adjusting unit 17 sets the set-up value by dividing the timings in order to adjust the amount of light emitted by the light emitter 10 and the bias voltage to cancel the DC offset signal.

Figure 9:
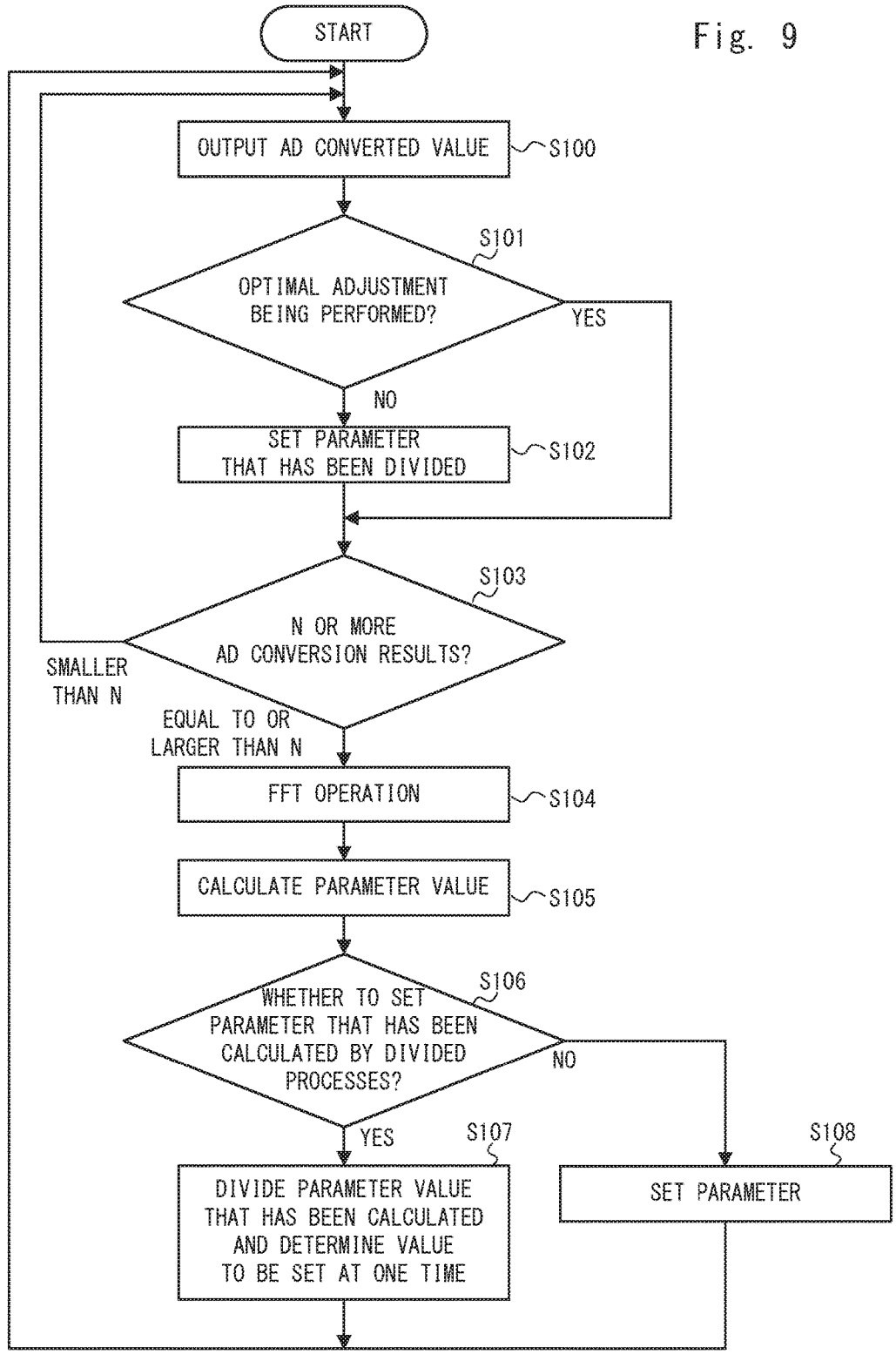
FIG. 9 is a flowchart showing one example of an adjustment operation in a pulsimeter according to a fourth embodiment.

FIG. 9 is a flowchart showing one example of the adjustment operation in the pulsimeter 1 according to this embodiment. In this embodiment, the adjusting unit 17 performs the adjustment by a conversion period by the AD converter 14 or a period when the frequency analysis is carried out by the frequency analyzing unit 15. The adjusting unit 17 executes, when the amount of adjustment is equal to or larger than a predetermined threshold, that is, when the difference between the set-up value that has been calculated and the current set-up value is equal to or larger than a predetermined threshold, the adjustment in the conversion period by the AD converter 14 in the divided processes. Further, when the amount of adjustment is smaller than the predetermined threshold, that is, when the difference between the set-up value that has been calculated and the current set-up value is smaller than the predetermined threshold, the adjusting unit 17 performs the adjustment at the analysis cycle of the frequency analyzing unit 15 without dividing the timings when the adjustment is performed. In the example shown in FIG. 9, the frequency analyzing unit 15 carries out FFT every time the AD converter 14 outputs N converted values.

Hereinafter, the flowchart shown in FIG. 9 will be described. In the following description, the set-up value that is set to adjust the amount of light emitted by the light emitter 10 and the set-up value to adjust the bias voltage for cancelling the DC offset signal are referred to as parameter values.

In Step 100 (S100), the AD converter 14 outputs one converted value.

In Step 101 (S101), it is determined whether the optimal adjustment is currently being performed. That is, it is determined whether the adjustment by the adjusting unit 17 is required. When the adjustment is required (No in S101), the process goes to Step 102. When the adjustment is not required (Yes in S101), the process goes to Step 103.

In Step 102 (S102), the adjusting unit 17 sets the parameter value that has been divided. Accordingly, the adjusting unit 17 performs the adjustment in the conversion period by the AD converter 14 in the divided processes. When there is no parameter value that has been divided, that is, when the adjustment is not performed in the divided processes, the adjusting unit 17 does not perform the adjustment in Step 102. The division of the parameter value will be described later.

In Step 103 (S103), it is determined whether the number of AD conversion results which will be analyzed by the frequency analyzing unit 15 has reached N. When the number of outputs of the converted value by the AD converter 14 is N or larger, the process goes to Step 104. On the other hand, when the number of outputs of the converted value by the AD converter 14 is smaller than N, it means that the number of pieces of data for the frequency analysis by the frequency analyzing unit 15 is insufficient. In this case, the process goes back to Step 100.

In Step 104 (S104), the frequency analyzing unit 15 performs the FFT operation on the result of the conversion by the AD converter 14.

In Step 105 (S105), the adjusting unit 17 calculates the parameter value based on the result of the analysis by the frequency analyzing unit 15. That is, the adjusting unit 17 determines the set-up value of the amount of light emitted by the light emitter 10 based on the result of the analysis by the frequency analyzing unit 15. Further, the adjusting unit 17 determines the set-up value of the bias voltage to cancel the DC offset signal based on the result of the analysis by the frequency analyzing unit 15.

Next, in Step 106 (S106), the adjusting unit 17 determines whether to set the parameter value calculated in Step 105 by divided processes. More specifically, the adjusting unit 17 determines whether the difference between the parameter value calculated in Step 105 and the parameter value that is currently set is equal to or larger than a predetermined threshold. When it is determined that the parameter value calculated in Step 105 should be set by the divided processes (Yes in Step 106), the process goes to Step 107. On the other hand, when it is not determined that the parameter value calculated in Step 105 should be set by the divided processes (No in Step 106), the process goes to Step 108.

In Step 107 (S107), the adjusting unit 17 divides the parameter value calculated in Step 105 and determines the value to be set at a time. For example, the adjusting unit 17 determines the amount of adjustment for each time to adjust the amount of adjustment by the parameter value calculated in Step 105 in a plurality of divided times. After Step 107, the process goes back to Step 100. Accordingly, in Step 102, the adjustment is performed in the divided processes.

On the other hand, in Step 108 (S108), the adjusting unit 17 sets the parameter value calculated in Step 105 and performs the adjustment. Accordingly, the adjustment is performed without dividing the process. After Step 108, the process goes back to Step 100.

As described above, in the pulsimeter 1 according to this embodiment, the adjustment is performed in the divided processes, whereby it is possible to suppress the distortion of the signal waveform due to the adjustment. Therefore, the occurrence of the spurious signal due to the adjustment is suppressed and the degradation in the measurement accuracy is suppressed. While the adjustment is performed in the divided processes when the amount of adjustment is equal to or larger than a predetermined threshold in the above description, the adjustment may be performed in the divided processes regardless of the magnitude of the amount of adjustment.

Figure 10:
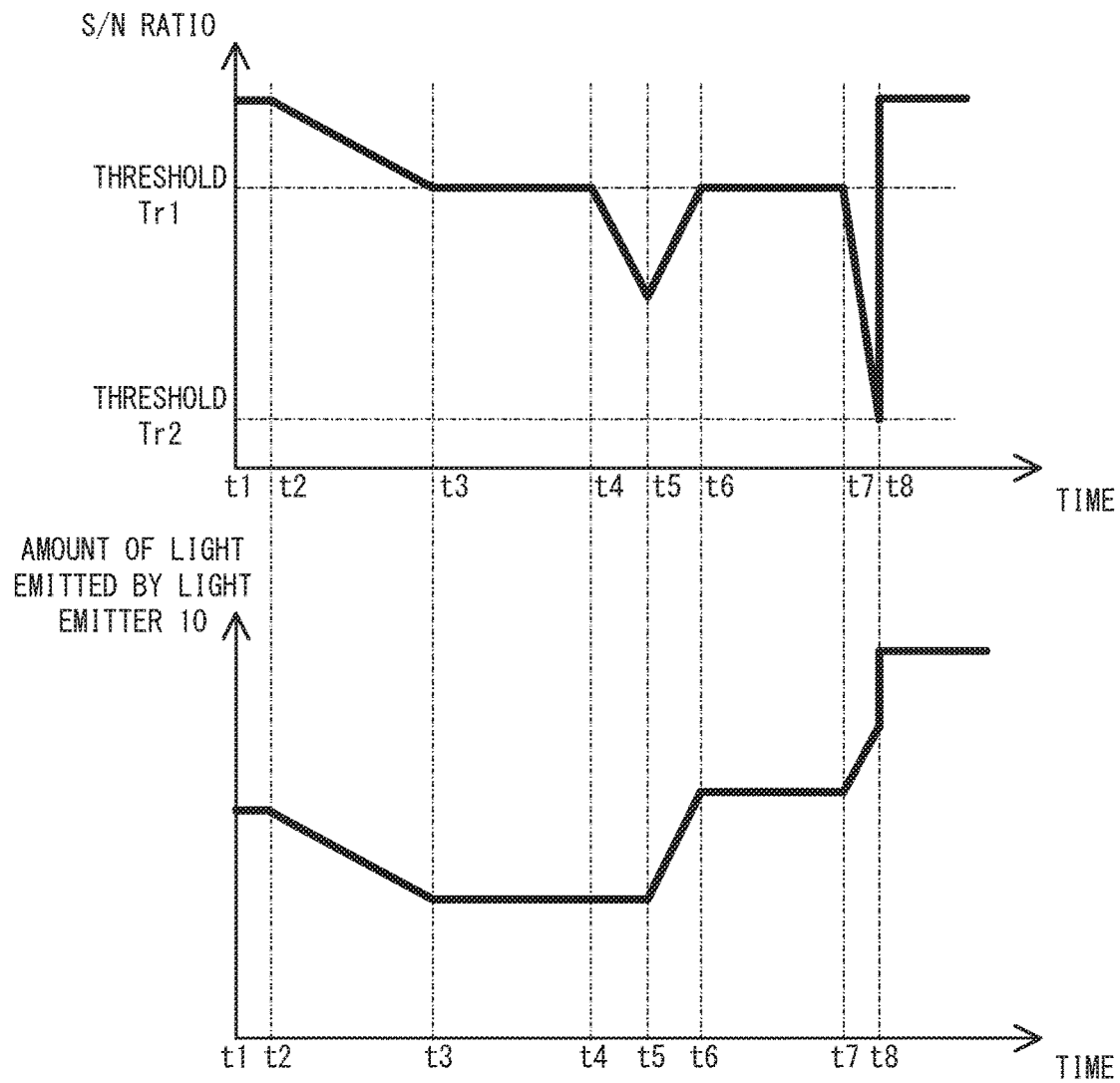
FIG. 10 is graphs showing one example of a temporal transition of an amount of light of a light emitter and an S/N ratio of a pulsation signal of the pulsimeter according to the fourth embodiment.

Now, one example of an operation of the pulsimeter 1 according to this embodiment is shown by temporal transitions of the amount of light emitted by the light emitter 10 and the S/N ratio of the pulsation signal. FIG. 10 is graphs showing one example of the temporal transitions of the amount of light emitted by the light emitter 10 and the S/N ratio of the pulsation signal of the pulsimeter 1 according to this embodiment. In the example shown in FIG. 10, at time t1 to t2, the S/N ratio of the pulsation signal is equal to or larger than a first threshold Tr1 and the amount of light emitted by the light emitter 10 is sufficiently large when the measurement is performed. In this case, the adjusting unit 17 adjusts the amount of light emitted by the light emitter 10 to decrease it in order to reduce the power consumption (time t2 to t3 in FIG. 10). The adjusting unit 17 performs the adjustment in such a way that the reduced amount of light for each time becomes within a range where a distortion does not occur in the signal waveform. That is, when the reduced amount based on the parameter value calculated in the above Step 105 is larger than the predetermined threshold, the adjusting unit 17 performs the adjustment of the reduced amount by dividing the process in a conversion period (that is, sampling period) of the AD converter 14. Assume, for example, that the range where a distortion does not occur in the signal is 10 LSB of the DA converter used to control the adjustment, the current set-up value is 20 LSB, and the value to be set is 50 LSB. In this case, when 30 LSB is set at one time, a distortion occurs in the signal waveform. Therefore, the adjusting unit 17 performs setting by three divided processes. When the setting is performed by several divided processes, it takes time for the expected setting to be completed. However, this causes no problem since it is important not to generate the distortion of the signal waveform due to the adjustment when the measurement is normally performed like at time t1.

The adjusting unit 17 determines, when the S/N ratio has reached the first threshold Tr1, that the amount of light emitted by the light emitter 10 is appropriate. In this case, the adjusting unit 17 neither increases nor decreases the amount of light emitted by the light emitter 10 and keeps the amount of light emitted by the light emitter 10 constant (time t3 to t4 and time t6 to t7 in FIG. 10). Further, when the S/N ratio becomes lower than the first threshold Tr1, the adjusting unit 17 performs the adjustment to make the S/N ratio the first threshold Tr1 without affecting the signal (time t4 to t5 and t5 to t6 in FIG. 10). The adjustment at this time is also performed in the divided processes as required. Degradation in the S/N ratio may occur when, for example, the distance between the photodetector 12 and the measurement target is deviated. Further, when the S/N ratio dramatically degrades and reaches a second threshold Tr2, the signal that has been measured is of no use. In this case, the adjusting unit 17 dramatically increases the amount of light emitted by the light emitter 10 and performs the measurement again (time t8 in FIG. 10). The adjustment in this case is performed, for example, as follows. That is, the amount of light may be increased by the amount corresponding to the adjustment width that has been calculated, as described in the second embodiment. Since data whose S/N ratio is lower than the second threshold Tr2 does not include pulse information, all the data are discarded.

Fifth Embodiment

Next, a fifth embodiment will be described. A description of the components already described above will be omitted. In this embodiment, a sample and hold circuit is included and the duration of a single light emission of the light emitter 10 is set according to a measurement value of time corresponding to the rising time of the photodetector 12 and the charge time of the sample and hold circuit.

Figure 11:
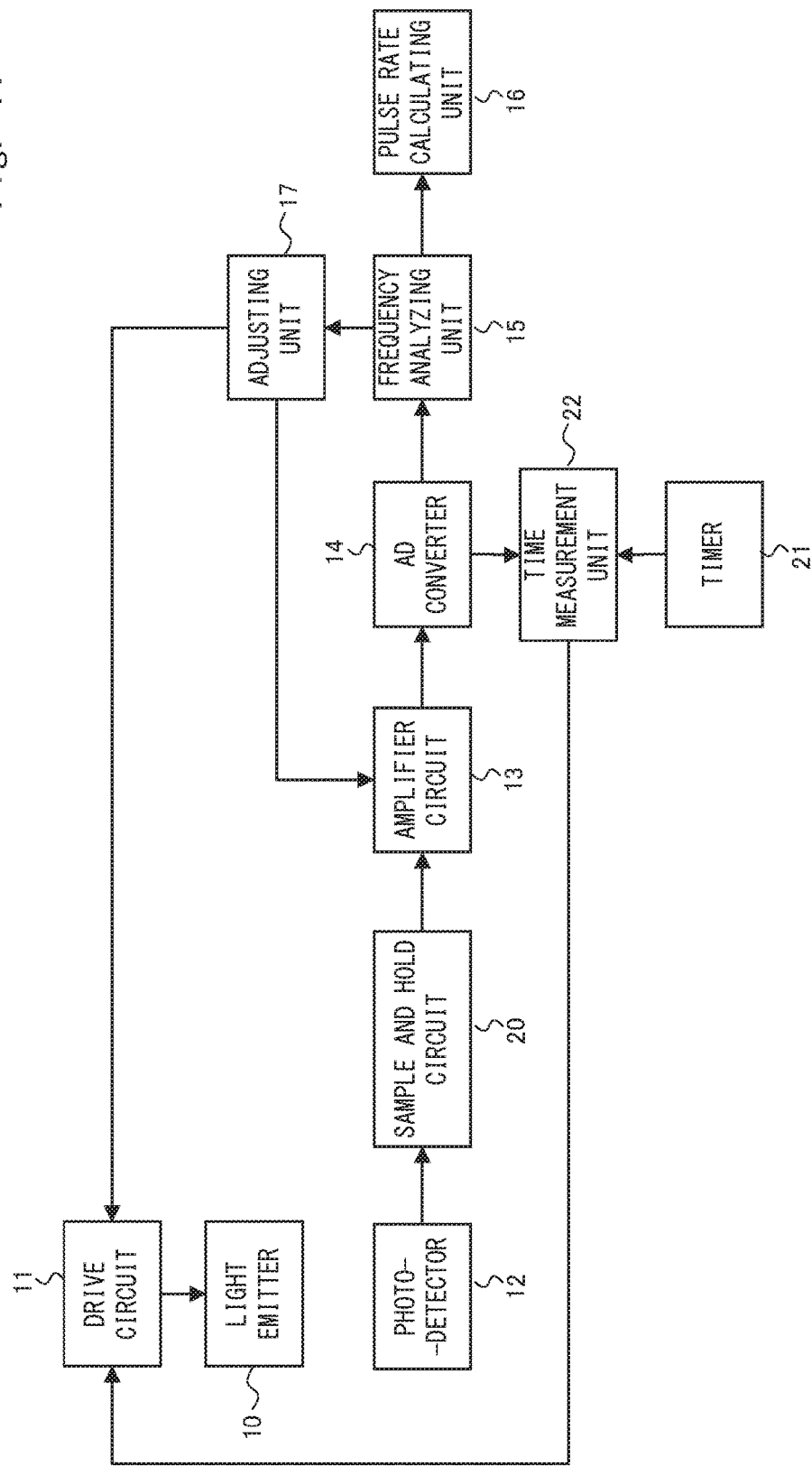
FIG. 11 is a block diagram showing a configuration of a pulsimeter according to a fifth embodiment.

FIG. 11 is a block diagram showing a configuration of a pulsimeter 2 according to this embodiment. The pulsimeter 2 includes a light emitter 10, a drive circuit 11, a photodetector 12, a sample and hold circuit 20, an amplifier circuit 13, an AD converter 14, a frequency analyzing unit 15, a pulse rate calculating unit 16, an adjusting unit 17, a timer 21, and a time measurement unit 22.

The sample and hold circuit 20 takes and holds, at a predetermined cycle, an output voltage of the photodetector 12 with respect to a light emission of the light emitter 10 at the predetermined cycle. Therefore, the AD converter 14 analog/digital converts the output voltage of the sample and hold circuit 20. More specifically, the AD converter 14 converts the analog signal obtained by amplifying the output of the sample and hold circuit 20 by the amplifier circuit 13. The sample and hold circuit 20 may, for example, be formed integrally with the MCU that implements the frequency analyzing unit 15 or it may be formed as a circuit provided outside of the MCU. The timer 21 is, for example, a timer included in the MCU and counts time. The time measurement unit 22 measures time from the start of the light emission of the light emitter 10 to the time for the output of the sample and hold circuit 20 to be constant. In this embodiment, specifically, the time measurement unit 22 measures, by the timer 21, the time from the start of the light emission of the light emitter 10 to the time for the output by the AD converter 14 to be constant after the light emission, whereby the time for the output of the sample and hold circuit 20 to be constant is measured. The time measurement unit 22 is implemented by the MCU, similar to, for example, the frequency analyzing unit 15 or the like.

One advantage of using the sample and hold circuit 20 is that it is possible to reduce the light emitting time of the light emitter 10. When the sample and hold circuit 20 is not used, the light emitting time of the light emitter 10 depends on the rising time of the photodetector 12 and the conversion time of the AD converter 14. In particular, when a high-accuracy measurement is performed, a digital sigma AD converter may be used as the AD converter 14. In this case, the conversion time becomes longer than that in the case in which another AD converter is used. Therefore, it is required to increase the light emitting time of the light emitter 10, which causes an increase in the power consumption. On the other hand, when the sample and hold circuit 20 is used, the light emitting time of the light emitter 10 can be limited to the rising time of the photodetector 12 and the charge time of the sample and hold circuit 20, whereby it is possible to reduce the power consumption.

As described above, the light emitting time of the light emitter 10 is preferably set to the sum of the rising time of the photodetector 12 and the charge time of the sample and hold circuit 20 in terms of power saving. The time of the sum of the rising time of the photodetector 12 and the charge time of the sample and hold circuit 20 is typically calculated by inference based on the specifications of components or the like. However, in reality, even when the photodetectors 12 of the same specifications are used, the rising time varies among the photodetectors 12. Therefore, when the light emitting time is set based on the specifications of the components or the like, light is emitted for a period of time longer than the actual time of the sum of the rising time of the photodetector 12 and the charge time of the sample and hold circuit 20. In this embodiment, the time corresponding to the rising time of the photodetector 12 and the charge time of the sample and hold circuit 20 is measured in the system that is actually used.

Specifically, the drive circuit 11 first causes the light emitter 10 to emit light. After the light emitter 10 emits light, the time measurement unit 22 monitors an output value of the AD converter 14. The time measurement unit 22 measures time from the start of the light emission of the light emitter 10 until the time the output by the AD converter 14 becomes constant using the timer 21. The time for the output by the AD converter 14 to be constant corresponds to the time for the output voltage of the sample and hold circuit 20 to be constant. Since the time measured by the time measurement unit 22 is the measurement value of the time corresponding to the rising time of the photodetector 12 and the charge time of the sample and hold circuit 20, the time measurement unit 22 sets the measured time as the duration of a single light emission of the light emitter 10. Therefore, the light emitter 10 is controlled such that the duration of the single light emission in the light emission repeated at a predetermined cycle, that is, a sampling period, becomes equal to the time measured by the time measurement unit 22.

Figure 12:
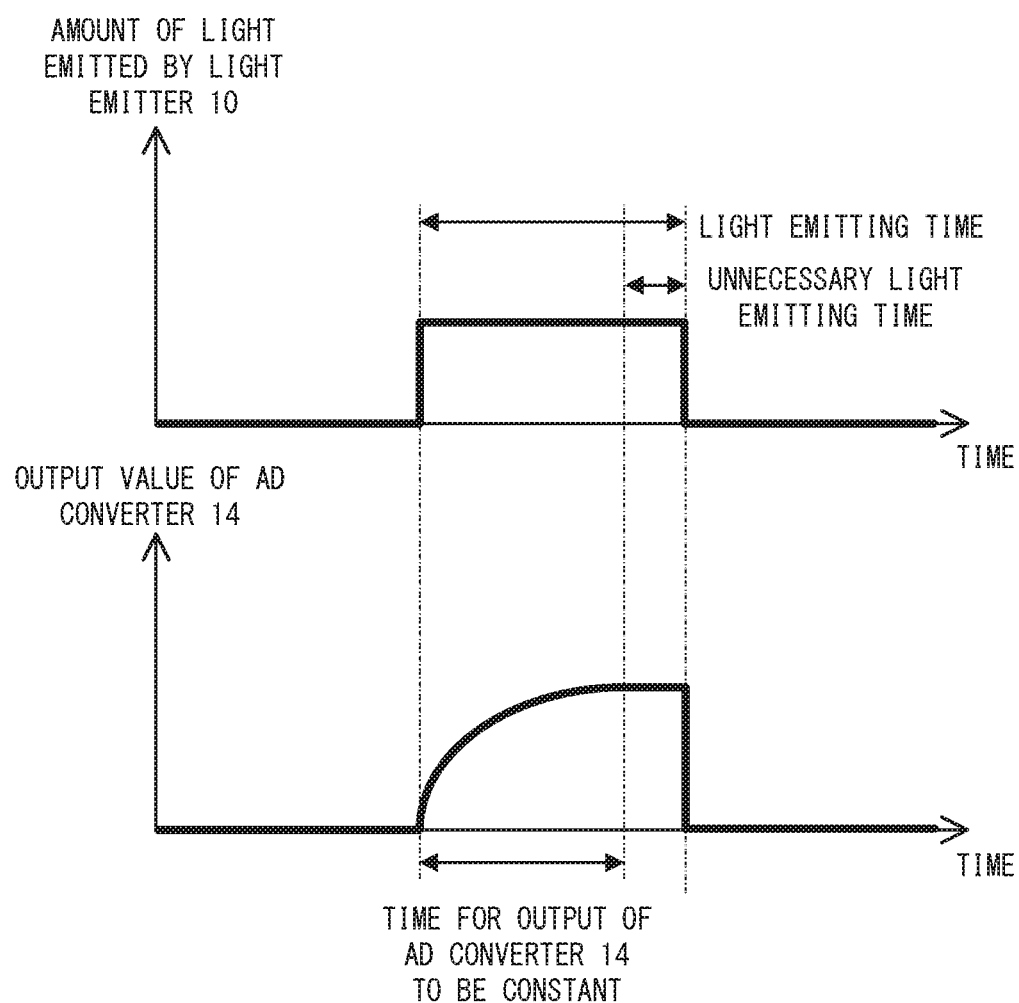
FIG. 12 is a diagram for describing setting of a light emitting time of a light emitter according to the fifth embodiment, with an upper graph showing a temporal transition of a light emission state of the light emitter and a lower graph showing a temporal transition of an output value of an AD converter when the light emitter emits light.

FIG. 12 is a diagram for describing setting of the light emitting time of the light emitter 10, with the upper graph indicating a temporal transition of the light emission state of the light emitter 10 and the lower graph indicating a temporal transition of the output value of the AD converter 14 when the light emitter 10 emits light. In FIG. 12, the light emitter 10 emits light for a period of time corresponding to the sum of the rising time of the photodetector 12 and the charge time of the sample and hold circuit 20 calculated based on the specifications of the photodetector 12 and the sample and hold circuit 20 or the like. As shown in FIG. 12, it is sufficient that the light emitter 10 emit light from the start of the light emission to the time until the time the output of the AD converter 14 becomes constant. Therefore, the light emission is not performed for a period of time longer than necessary. It is therefore possible to suppress the power consumption. While the pulsimeter 2 includes the timer 21 and the time measurement unit 22 in this embodiment, it is sufficient that the duration of a single light emission be set according to the measurement value of the time corresponding to the rising time of the photodetector 12 and the charge time of the sample and hold circuit 20 in the light emitter 10. It is not necessary to include timer 21 and the time measurement unit 22. Further, while the time measurement unit 22 monitors the output of the AD converter 14 used to measure the pulse in this embodiment, it may monitor an output of an AD converter that receives the output voltage of the sample and hold circuit 20 (e.g., the output of the amplifier circuit 13) other than the AD converter 14. Further, when an AD converter in which a high-speed operation is possible other than the AD converter 14 is used, it is possible to measure time more finely. Since the AD converter is used to determine whether the output has exceeded a predetermined value, the accuracy of the AD converter may be lower than that of the AD converter 14.

Next, a circuit configuration according to this embodiment will be described. When the amount of light emitted by the light emitter 10 is controlled, it is required to provide a DA converter that digital/analog converts a control signal that controls the amount of light. Further, when the DC offset signal is cancelled from the biometric signal acquired via the photodetector 12, it is required to provide a DA converter that digital/analog converts the control signal that generates the bias voltage to be input to the amplifier circuit 13. However, a general MCU does not usually include two or more DA converters. Therefore, a technique for using one DA converter and one operational amplifier to control both the amount of light and the bias voltage will be proposed.

Figure 13:
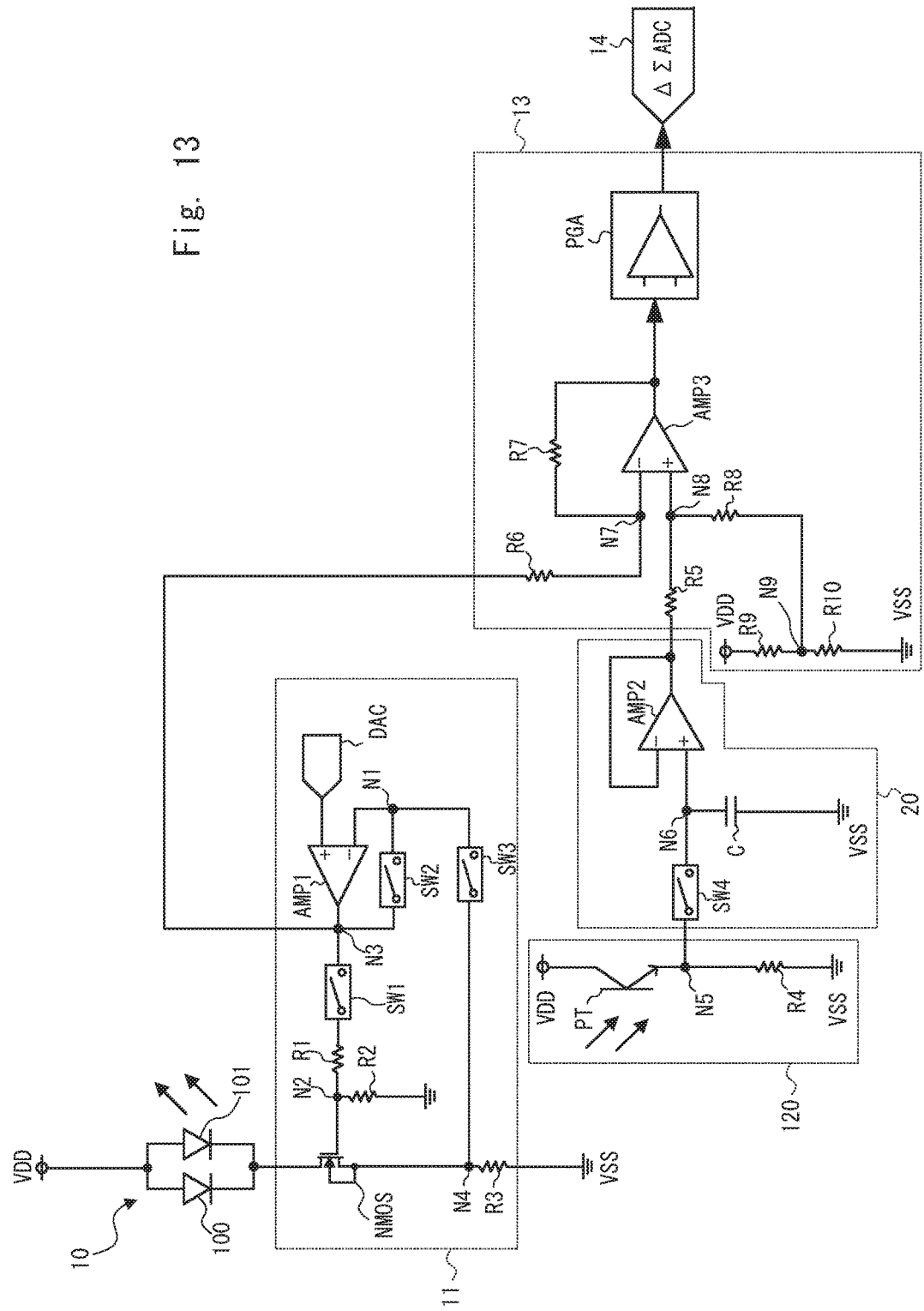
FIG. 13 is a circuit diagram showing one example of a circuit configuration of the pulsimeter according to the fifth embodiment.

FIG. 13 is a circuit diagram showing one example of the circuit configuration of the pulsimeter 2 according to this embodiment. In the example shown in FIG. 13, among the components forming the pulsimeter 2, the light emitter 10, the drive circuit 11, a light receiving sensor circuit 120, the sample and hold circuit 20, the amplifier circuit 13, and the AD converter 14 are shown.

The light emitter 10 is formed of LEDs 100 and 101. The LEDs 100 and 101 are connected in parallel between a line of a power supply voltage VDD and a line of a ground voltage VSS. More specifically, the LEDs 100 AND 101 each have one terminal connected to the line of the power supply voltage VDD and the other terminal connected to the drain of an N-channel MOS transistor NMOS that forms the drive circuit 11.

The drive circuit 11 includes a DA converter DAC, an operational amplifier AMP1, switches SW1, SW2, and SW3, resistance elements R1, R2, and R3, and an N-channel MOS transistor NMOS. The drive circuit 11 has, besides the function as a circuit that drives the light emitter 10, the function as a circuit that generates a bias voltage to be supplied to the amplifier circuit 13. These functions are switched by changing the switches SW1, SW2, and SW3.

The DA converter DAC is, for example, a 12-bit DA converter. The DA converter DAC receives a digital control signal that controls the amount of light or a digital control signal that digitally controls the bias voltage, converts the digital control signal that has been input to the DA converter DAC into an analog signal, and outputs the converted signal to the non-inverting input terminal of the operational amplifier AMP1. The inverting input terminal of the operational amplifier AMP1 is connected to a node N1. The output terminal of the operational amplifier AMP1 is connected to the switch SW1. The switch SW1 is connected to the gate of the N-channel MOS transistor NMOS via the resistance element R1. Further, a node N2 provided between the resistance element R1 and the N-channel MOS transistor NMOS is connected to the line of the ground voltage VSS via the resistance element R2. The source of the N-channel MOS transistor NMOS is connected to the line of the ground voltage VSS via the resistance element R3.

Further, the switch SW2 has one terminal connected to the node N1 and the other terminal connected to a node N3 provided between the operational amplifier AMP1 and the switch SW1. That is, the switch SW2 has one terminal connected to the inverting input terminal of the operational amplifier AMP1 via the node N1 and the other terminal connected to the output terminal of the operational amplifier AMP1 via the node N3. Therefore, when the switch SW2 is ON, a negative feedback loop of the operational amplifier AMP1 is formed. The node N3 is further connected to the amplifier circuit 13.

The switch SW3 has one terminal connected to the node N1 and the other terminal connected to anode N4 provided between the source of the N-channel MOS transistor NMOS and the resistance element R3.

When a control signal that adjusts the amount of light emitted by the light emitter 10 is input to the DA converter DAC, the switch SW1 is turned on, the switch SW3 is turned on, the switch SW2 is turned off, and the operational amplifier AMP1, the switches SW1 and SW3, the resistance elements R1, R2, and R3, and the N-channel MOS transistor NMOS form a constant current drive circuit.

Further, when the control signal that controls the bias voltage to be supplied to the amplifier circuit 13 is input to the DA converter DAC, the switch SW1 is turned off, the switch SW3 is turned off, the switch SW2 is turned on, and the operational amplifier AMP1 and the switch SW2 form a buffer circuit to supply the bias voltage generated according to the control signal to the amplifier circuit 13.

As described above, the switches SW1, SW2, and SW3 switch a light emission control state (first state), which is a state in which the operational amplifier AMP1 is used as the constant current drive circuit to drive the light emitter 10 based on the signal to control the amount of light and a bias voltage generation state (second state), which is a state in which the operational amplifier AMP1 is used as the buffer circuit to supply the bias voltage generated based on the signal to control the bias voltage to the amplifier circuit 13. It is therefore possible to use one operational amplifier AMP1 and one DA converter DAC to control both the amount of light and the bias voltage. It is therefore possible to suppress the number of components. Further, when the bias voltage is supplied to the amplifier circuit 13, the operational amplifier AMP1 is used as a buffer amplifier. Therefore, the output of the DA converter DAC is in a low-impedance state, whereby it is possible to suppress the influence of the resistance value of the DA converter DAC on the gain of the amplifier circuit 13.

The light receiving sensor circuit 120 includes a photo transistor PT as the photodetector 12 and a resistance element R4, and the photo transistor PT and the resistance element R4 are connected in series between the line of the power supply voltage VDD and the line of the ground voltage VSS. A node N5 is provided between the photo transistor PT and the resistance element R4 and the node N5 is connected to the sample and hold circuit 20. The light receiving sensor circuit 120 outputs the light receiving signal to the sample and hold circuit 20 via the node N5.

The sample and hold circuit 20 includes a switch SW4, an operational amplifier AMP2, and a capacitor C, which is a capacitative element. The switch SW4 has one terminal connected to the node N5 of the light receiving sensor circuit 120 and the other terminal connected to the non-inverting input terminal of the operational amplifier AMP2. Further, a node N6 is provided between the switch SW4 and the non-inverting input terminal of the operational amplifier AMP2. The capacitor C is provided between the node N6 and the line of the ground voltage VSS. Therefore, while the light receiving sensor circuit 120 outputs the light receiving signal and the switch SW4 is ON, the capacitor C is charged to the output voltage of the light receiving sensor circuit 120. The capacitor C supplies the output voltage of the light receiving sensor circuit 120 during charging to the operational amplifier AMP2 even when the switch SW4 is turned off. In the operational amplifier AMP2, a negative feedback loop is formed. At the same time, the output terminal of the operational amplifier AMP2 is connected to a resistance element R5 of the amplifier circuit 13. In the sample and hold circuit 20 having the above configuration, the switch SW4 is controlled in accordance with the light emitting period of the light emitter 10.

The amplifier circuit 13 includes an operational amplifier AMP3, a programmable instrumentation amplifier PGA, and resistance elements R5, R6, R7, R8, R9, and R10. The inverting input terminal of the operational amplifier AMP3 is connected to the node N3 of the drive circuit 11 via the resistance element R6. Further, the output terminal of the operational amplifier AMP3 is connected to a node N7 provided between the inverting input terminal of the operational amplifier AMP3 and the resistance element R6 via the resistance element R7, and a negative feedback loop is formed. The non-inverting input terminal of the operational amplifier AMP3 is connected to the output terminal of the sample and hold circuit 20 via the resistance element R5. A node N8 is provided between the non-inverting input terminal of the operational amplifier AMP3 and the resistance element R5 and the non-inverting input terminal of the operational amplifier AMP3 is connected to the resistance element R8 via the node N8. The resistance element R8 has one terminal connected to the node N8 and the other terminal connected to a node N9 provided between the resistance element R9 and the resistance element R10. The resistance elements R9 and R10 are connected in series between the line of the power supply voltage VDD and the line of the ground voltage VSS and form a voltage dividing circuit. According to the above configuration, the operational amplifier AMP3 forms a differential amplifier circuit and cancels the DC offset signal included in the signal output from the sample and hold circuit 20 based on the bias voltage input via the node N3. When the pulsimeter 2 is switched to the bias voltage generation state as described above, a buffer circuit is formed, whereby the error of the gain of the differential amplifier circuit can be reduced. The output terminal of the operational amplifier AMP3 is connected to the input terminal of the programmable instrumentation amplifier PGA. The programmable instrumentation amplifier PGA is an amplifier which can change the gain by the aforementioned adjusting unit 17. The output of the programmable instrumentation amplifier PGA is input to the AD converter 14. The AD converter 14 is, for example, a digital sigma AD converter, and analog/digital converts the signal output from the programmable instrumentation amplifier PGA.

Figure 14:
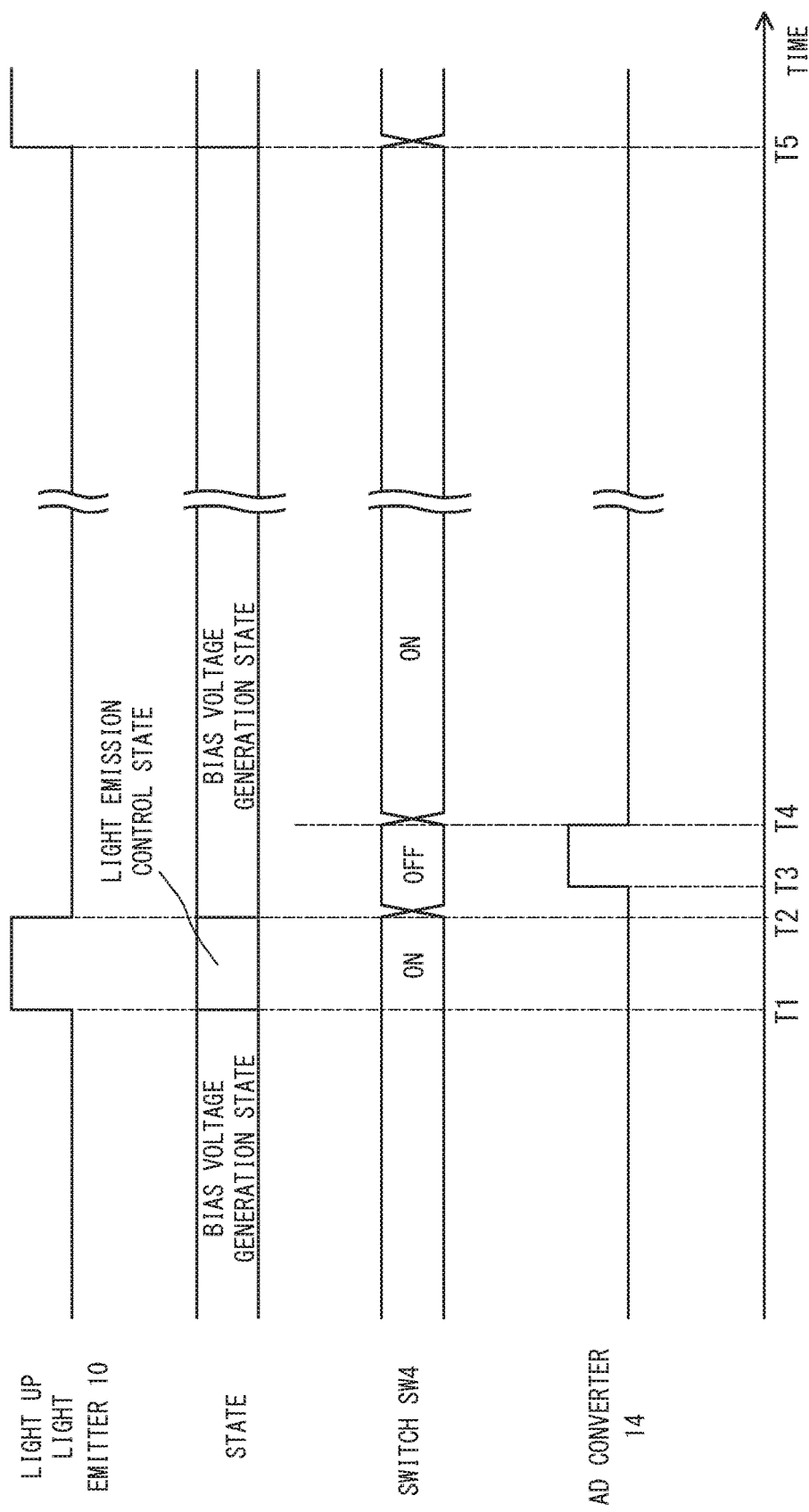
FIG. 14 is a time chart showing one example of a timing when a light emission control state and a bias voltage generation state are switched in the pulsimeter according to the fifth embodiment.

FIG. 14 is a time chart showing one example of the timing when the light emission control state and the bias voltage generation state are switched in the pulsimeter 2. FIG. 14 shows a time chart of one sampling operation in the pulsimeter 2. In the example shown in FIG. 14, it is assumed that the light emitter 10 emits light from time T1 to time T2.

At time T1, the light emitter 10 is lighted up. At this time, the pulsimeter 2 is switched from the bias voltage generation state to the light emission control state. That is, at time T1, the switch SW1 and the switch SW3 are switched from OFF to ON and the switch SW2 is switched from ON to OFF. Then, at time T2, the light emitter 10 is extinguished. At this time, the pulsimeter 2 is switched from the light emission control state to the bias voltage generation state. That is, at time T2, the switch SW1 and the switch SW3 are switched from ON to OFF and the switch SW2 is switched from OFF to ON. Further, at time T2, the switch SW4 is switched from ON to OFF. Time T1 to time T2 are time during which the sampling operation of the sample and hold circuit 20 is performed and the capacitor C is charged by the output of the light receiving sensor circuit 120. After that, at time T3, the AD converter 14 starts the conversion. Time T2 to time T3 correspond to a predetermined waiting time to wait for the settling time of the analog front end. Concretely, the waiting time occurs when, for example, the light emission control state is switched to the bias voltage generation state. At time T4, the switch SW4 is turned on and the AD converter 14 completes the conversion. The capacitor C maintains the charging state until the time the switch SW4 is turned off at time T4. That is, time T2 to time T4 are time during which a hold operation of the sample and hold circuit 20 is performed. When the switch SW4 is turned on at time T4, the capacitor C starts a discharge operation. At time T5, the light emitter 10 again emits light, and the above operation is repeated in the pulsimeter 2.

While the invention made by the present inventors has been specifically described based on the embodiments, it is needless to say that the present invention is not limited to the embodiments already stated above and various changes may be made on the embodiments without departing from the spirit of the present invention.

For example, while the pulsimeter 1 including the amplifier circuit 13 is shown in FIG. 1 and the example in which the adjusting unit 17 adjusts the amount of light emitted by the light emitter 10 and the gain of the amplifier circuit 13 has been described in FIG. 1, the pulsimeter 1 does not necessarily include the amplifier circuit 13 when the adjusting unit 17 does not perform gain adjustment.

Figure 15:
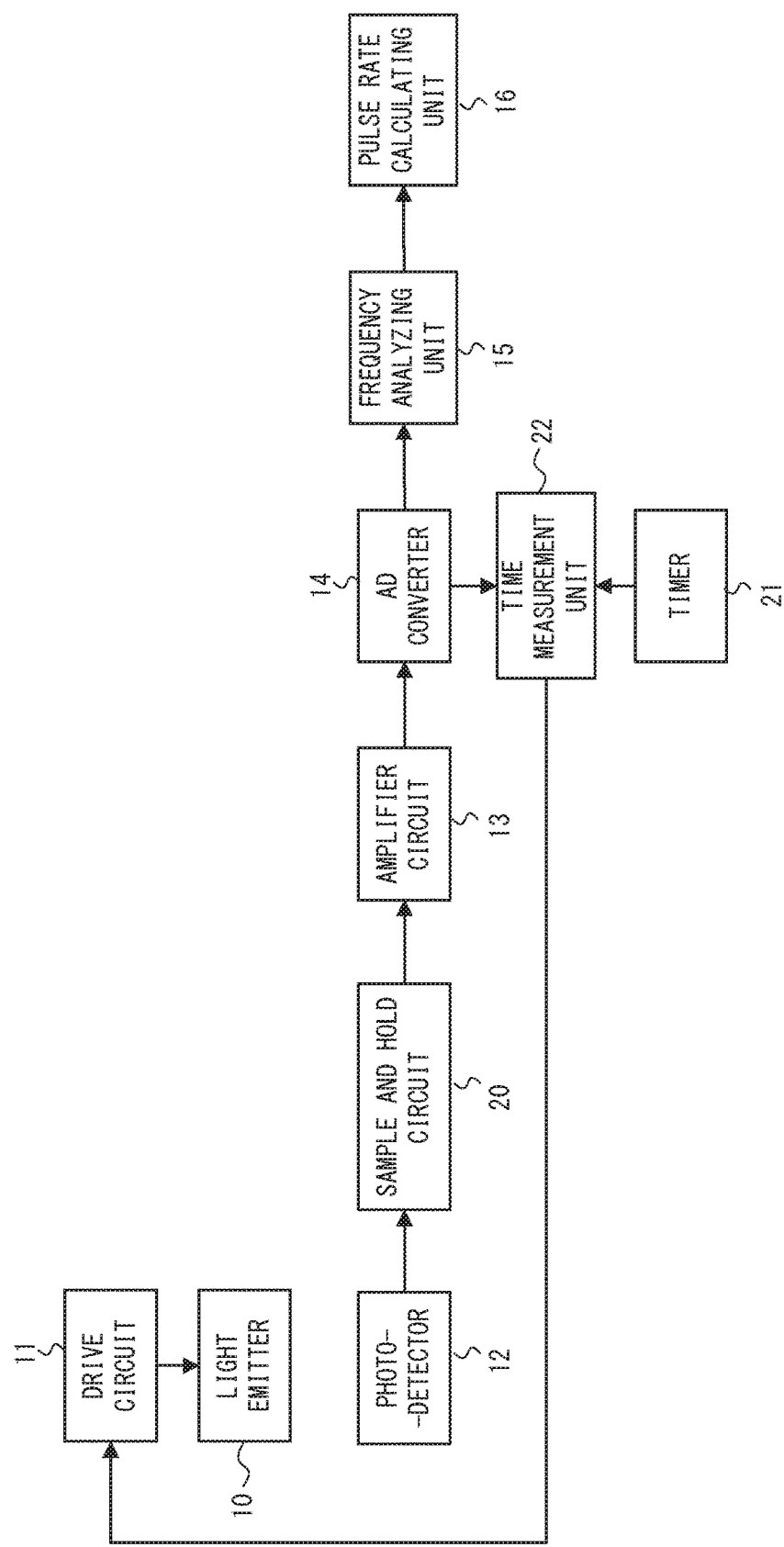
FIG. 15 is a block diagram showing another configuration of the pulsimeter according to the fifth embodiment.

Further, while the configuration of the pulsimeter 2 according to the fifth embodiment is shown in FIG. 11, the adjusting unit 17 may not be provided in the pulsimeter 2. That is, the pulsimeter 2 may be formed as shown in FIG. 15. When the output from the sample and hold circuit 20 is sufficient, the amplifier circuit 13 may be omitted. Further, as described above, in the pulsimeter 2, it is sufficient that the light emitting time of the light emitter 10 be set according to the measurement value. The pulsimeter 2 may not necessarily include the timer 21 and the time measurement unit 22. As stated above, in the pulsimeter 2 according to the fifth embodiment, the adjusting unit 17 may not be provided or the configuration of the adjusting unit 17 described in the first to fourth embodiments may be provided.

Further, while the configuration in which the pulsation signal is acquired from the reflective sensor shown in FIG. 2 is employed in the above embodiments, a transmission type sensor that emits light to a finger, receives light that has passed the finger on a side opposite to the light emitting side, and acquires the pulsation signal may be used. Further, the measurement target is not limited to the human body and may be animals. Further, the measurement site may be other than the finger and may be an arm, a palm, or a foot. Further, the present invention may be applied to a measurement of a pulse in a pulse oxymeter.

The first to fifth embodiments can be combined as desirable by one of ordinary skill in the art.

While the invention has been described in terms of several embodiments, those skilled in the art will recognize that the invention can be practiced with various modifications within the spirit and scope of the appended claims and the invention is not limited to the examples described above.

Further, the scope of the claims is not limited by the embodiments described above.

Furthermore, it is noted that, Applicant's intent is to encompass equivalents of all claim elements, even if amended later during prosecution.

What is claimed is:

1. A pulsimeter comprising:
   a light emitter configured to be driven by a drive circuit and further configured to emit light to a blood vessel of a measurement target;

a photodetector configured to detect light emitted by the light emitter via the blood vessel;

an analog/digital converter configured to receive and analog/digital convert an output signal from the photodetector;

a frequency analyzing unit configured to receive and frequency analyze data from the analog/digital converter and further to filter a DC offset signal from the data, by canceling the DC offset signal from the data, based on a result of frequency-analyzing the data; and an adjusting unit configured to adjust an amount of light emitted by the light emitter based on at least one frequency component of the data, received from the frequency analyzing unit, from which the DC offset signal is filtered.

2. The pulsimeter according to claim 1, further comprises an amplifier circuit configured to receive and amplify the output signal from the photodetector, wherein:

the analog/digital converter is further configured to analog/digital convert a signal amplified by the amplifier circuit, and the adjusting unit is further configured to adjust the amount of light emitted by the light emitter or a gain of the amplifier circuit based on the result of the analysis by the frequency analyzing unit.

3. The pulsimeter according to claim 2, wherein the adjusting unit is further configured to adjust a bias voltage input to the amplifier circuit based on the result of the analysis by the frequency analyzing unit.

4. The pulsimeter according to claim 1, wherein the adjusting unit is further configured to compare an S/N ratio with a predetermined threshold and to perform an adjustment according to the comparison result.

5. The pulsimeter according to claim 1, wherein the adjusting unit is further configured to determine an amount of light emitted by the light emitter to achieve a target evaluation value from a first evaluation value regarding a strength of a pulsation signal when the light emitter emits light with a first amount of light, a second evaluation value regarding the strength of the pulsation signal when the light emitter emits light with a second amount of light, and a predetermined target evaluation value regarding the strength of the pulsation signal, and to adjust the amount of light emitted by the light emitter based on the calculation result.

6. The pulsimeter according to claim 1, wherein the adjusting unit is further configured to perform adjustment at a predetermined cycle in a case in which the amount of light emitted by the light emitter is adjusted to increase it and is larger than an adjustment by the adjusting unit performed at the predetermined cycle in a case in which the amount of light emitted by the light emitter is adjusted to decrease it.

7. The pulsimeter according to claim 1, wherein the adjusting unit is further configured to determine a set-up value for the adjustment at a predetermined cycle and to execute the adjustment of the set-up value in a plurality of divided times within the predetermined cycle.

8. The pulsimeter according to claim 7, wherein the adjusting unit is further configured to determine the set-up value at an analysis cycle by the frequency analyzing unit and to execute the adjustment of the set-up value in a plurality of divided times according to a conversion period by the analog/digital converter.

9. The pulsimeter according to claim 1, wherein the photodetector is further configured to detect light from the light emitter reflected in the blood vessel.

10. The pulsimeter according to claim 1, wherein the frequency analyzing unit is further configured to perform the frequency analysis by Fast Fourier Transform.

11. The pulsimeter according to claim 1, wherein the frequency analyzing unit is further configured to filter the DC offset signal by Fourier transforming the data and subsequently filtering the DC offset signal as a signal satisfying a first predetermined frequency condition and by not filtering the at least one frequency component as a second signal satisfying a second predetermined frequency condition, the first predetermined frequency condition being a determination whether a first portion of the data comprises a component at 0 Hz, and the second predetermined frequency condition being a determination whether a second portion of the data comprises a component between 0.5 and 2 Hz.

12. The pulsimeter according to claim 11, further comprises an amplifier circuit configured to receive and amplify the output signal from the photodetector, wherein the amplifier circuit is further configured to receive an indication from the adjusting unit, the indication controlling the amplifier circuit to amplify the second portion of the data without amplifying the first portion of the data.

13. An adjustment method of a pulsimeter comprising:
emitting light to a blood vessel of a measurement target, the emitting controlled by a drive circuit;
detecting light via the blood vessel;
analog/digital converting a detection signal of the light;
frequency-analyzing data that has been analog/digital converted;
filtering a DC offset signal from the data, by canceling the DC offset signal from the data, based on a result of frequency-analyzing the data; and
adjusting an amount of light of the light emitted to the blood vessel based on at least one frequency component of the data from which the DC offset signal is filtered.

14. The adjustment method of the pulsimeter according to claim 13, comprising calculating an amount of light of a light emitter to achieve a target evaluation value from a first evaluation value regarding a strength of a pulsation signal when the light emitter emits light with a first amount of light, a second evaluation value regarding the strength of the pulsation signal when the light emitter emits light with a second amount of light, and a predetermined target evaluation value regarding the strength of the pulsation signal, and adjusting the amount of light emitted by the light emitter based on the calculation result.

15. The adjustment method of the pulsimeter according to claim 13, wherein the adjustment is performed at a predetermined cycle in a case in which the amount of light is adjusted to increase it and is larger than an adjustment performed at the predetermined cycle in a case in which the amount of light is adjusted to decrease it.

16. The adjustment method of the pulsimeter according to claim 13, comprising determining a set-up value for the adjustment of the amount of light emitted to the blood vessel at a predetermined cycle and executing the adjustment of the set-up value in a plurality of divided times within the predetermined cycle.

* * * * *